(12) United States Patent
Fréchet et al.

(10) Patent No.: US 6,616,825 B1
(45) Date of Patent: Sep. 9, 2003

(54) ELECTROCHROMATOGRAPHIC DEVICE FOR USE IN ENANTIOSELECTIVE SEPARATION, AND ENANTIOSELECTIVE SEPARATION MEDIUM FOR USE THEREIN

(75) Inventors: Jean M. J. Fréchet, Oakland, CA (US); Frantisek Svec, Alameda, CA (US); Michael Lämmerhofer, Vienna (AT)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/645,079

(22) Filed: Aug. 23, 2000

(51) Int. Cl.$^7$ .................. G01N 27/453; C02F 1/28; C08F 2/46; C08F 34/04; C08F 32/08
(52) U.S. Cl. ................ 204/605; 204/469; 210/656; 522/6; 526/256; 526/259; 526/260; 526/318.44; 526/320
(58) Field of Search ................ 204/601, 605, 204/606, 469; 422/70; 522/6, 13; 526/256, 259, 260, 307, 317.1, 318.44, 319, 320, 328; 210/656

(56) References Cited

U.S. PATENT DOCUMENTS

| | | | |
|---|---|---|---|
| 3,796,578 A | * 3/1974 | Hosoi et al. | 430/280.1 |
| 5,334,310 A | 8/1994 | Frechet et al. | 210/198.2 |
| 5,376,252 A | * 12/1994 | Ekstrom et al. | 204/603 |
| 5,453,185 A | 9/1995 | Frechet et al. | 210/198.2 |
| 5,728,457 A | 3/1998 | Frechet et al. | 428/310.5 |
| 6,013,738 A | * 1/2000 | Daly et al. | 210/198.2 |

FOREIGN PATENT DOCUMENTS

WO    WO 97/46557    12/1997

OTHER PUBLICATIONS

Ericson et al. (1999), "Reversed–Phase Electrochromatography of Proteins on Modified Continuous Beds Using Normal–Flow and Counterflow Gradients. Theoretical and Practical Considerations," *Analytical Chemistry* 71(8):1621–1627. Apr.

Fujimoto et al. (1995), "Capillary Electrochromatography of Small Molecules in Polyacrylamide Gels with Electroosmotic Flow," *Journal of Chromatography A* 716:107–113. Month unknown.

Fujimoto et al. (1996), "Fritless Packed Columns for Capillary Electrochromatography: Separation of Uncharged Compounds in Hydrophobic Hydrogels," *Analytical Chemistry* 68:(17):2753–2757. Sep.

Gusev et al. (1999), "Capillary Columns with In Situ Formed Porous Monolithic Packing for Micro High–Performance Liquid Chromatography and Capillary Electrochromatography," *Journal of Chormatography A* 855:273–290. Month unknown.

Hjertén (1999), "Standard and Capillary Chromatography, Including Electrochromatography, on Continuous Polymer Beds (Monoliths), Based on Water–Soluble Monomers," *Ind. Eng. Chem. Res.* 38(4):1205–1214. Month unknown.

(List continued on next page.)

*Primary Examiner*—Nam Nguyen
*Assistant Examiner*—Alex Noguerola
(74) *Attorney, Agent, or Firm*—Reed & Eberle LLP; Dianne E. Reed; Louis L. Wu

(57) ABSTRACT

An electrochromatographic device is provided for conducting enantioselective separation of enantiomers. The device is comprised of a conduit containing a monolithic enantioselective separation medium, and may be, for example, a capillary tube or a microchannel in a substrate. The enantioselective separation medium is prepared by copolymerization of (a1) an ionizable chiral monomer or (a2) a chiral monomer and an ionizable comonomer, along with (b) a crosslinking comonomer and (c) a polymerization initiator, in (d) a porogenic solvent. Following ionization, the enantioselective separation medium serves as a charge carrier as well as a chiral separation medium, and further acts as an electroosmotic pump to facilitate the flow of a fluid. The invention also provides methods for preparing the enantioselective separation medium and electrochromatographic devices fabricated therewith.

49 Claims, 9 Drawing Sheets

OTHER PUBLICATIONS

Kiode et al. (2000), "Enantiomeric Separations if Acidic and Neutral Compounds by Capillary Electrochromatography with β–Cyclodextrin–Bonded Positively Charged Polyacrylamide Gels," *J. High Resol. Chromatogr.* 23(1):59–66. Month unknown.

Lämmerhofer et al. Jun. (2000), "New Generation of Monolithic Stationary Phases for Enantioselective Capillary Electrochromatography," 23$^{rd}$ *International Symposium on Capillary Chromatography*, Riva del Garda, Italy.

Lämmerhofer et al. (2000), "Macroporous Monolithic Chiral Stationary Phases Based on Quinidine Carbamate for Enantioselective Capillary Electrochromatography," *HPLC 2000*, Seattle (abstract only). Jun.

Lewandowski et al. (1999), "A Combinatorial Approach to Recognition of Chirality: Preparation of Highly Enantioselective Aryl–Dihydropyrimidine Selectors for Chiral HPLC," *Journal of Combinatorial Chemistry* 1(1):105–112. Month unknown.

Laio et al. (1996), "Preparation of Continuous Beds Derivatized with One–Step Alkyl and Sulfonate Groups for Capillary Electrochromatography," *Analytical Chemistry* 68(19):3468–3472. Oct.

Murer et al. (1999), "On–Bead Combinatorial Approach to the Design of Chiral Stationary Phases for HPLC," *Analytical Chemistry* 71(7):1278–1284. Month unknown.

Nilsson et al. (1994), "Imprinted Polymers as Antibody Mimetics and New Affinity Gels for Selective Separations in Capillary Electrophoresis," *Journal of Chromatography A* 680:57–61. Month unknown.

Palm et al. (1997), "Macroporous Polyacrylamide/Poly(Ethylene Glycol) Matrixes as Stationary Phases in Capillary Electrochromatography," *Analystical Chemistry* 69(22):4499–4507. Nov.

Peters et a. (1997), "Molded Rigid Polymer Monoliths as Separation Media for Capillary Electrochromatography," *Analytical Chemistry* 69(17):3646–3649. Sep.

Peters et al. (1998), "Molded Rigid Polymer Monoliths as Separation Media for Capillary Electrochromatography. 1. Fine Control of Porous Properties and Surface Chemistry," *Analytical Chemistry* 70(11):2288–2295. Jun.

Peters et al. (1998), "Molded Rigid Polymer Monoliths as Separation Media for Capillary Electrochromatography. 2. Effect of Chromatographic Conditions on the Separation," *Analytical Chemistry* 70(11):2296–2302. Jun.

Peters et al. (1998), "Chiral Electrochromatography with a 'Moulded' Rigid Monolithic Capillary Column," *Analytical Communications* 35 83–86. Mar.

Schweitz et al. (1997), "Capillary Electrochromatography with Predetermined Selectivity Obtained through Molecular Imprinting," *Analytical Chemistry* 69(6):1179–1183. Mar.

Schweitz et al. (1998), "Molecular Imprint–Based Stationary Phases for Capillary Electrochromatography," *Journal of Chromatography A* 817:5–13. Month unknown.

Svec et al. (2000), "Monolithic Stationary Phases for Capillary Electrochromatography Based on Synthetic PolymersL Designs and Applications," *J. High. Resol. Chromatogr.* 23(1):3–18. Month unknown.

Svec et al. (2000), "Design of the Monolithic Polymers Used in Capillary Electrochromatography Columns," *Journal of Chromatography A* 887:3–29. Month unknown.

Svec Apr. (2000), "Towards Monolithic Stationary Phases for Electrochromatography on a Microchip," *Analytica*, Munich, Germany (abstract only).

Xiong et al. (2000), "Capillary Electrochromatography with Monolithic Poly(Styrene–co–Divinylbenzene–co–Methacrylic Acid) as the Stationary Phase," *J. High Resol. Chromatogr.* 23(1):67–72. Month unknown.

* cited by examiner

ELECTROCHROMATOGRAPHIC DEVICE FOR USE IN ENANTIOSELECTIVE SEPARATION, AND ENANTIOSELECTIVE SEPARATION MEDIUM FOR USE THEREIN

ACKNOWLEDGEMENT OF GOVERNMENT SUPPORT

This invention was made with government support under Grant (or Contract) No. GM48364 awarded by the National Institutes of Health. The U.S. government has certain rights in this invention.

TECHNICAL FIELD

This invention relates generally to the field of electrochromatographic separation, and more particularly relates to a novel enantioselective separation medium comprised of a monolithic, chiral, ionizable copolymer.

BACKGROUND

The original promise of electrochromatography to improve the efficiency of liquid chromatography by using an electrical field to achieve plug-like electroosmotic flow (EOF) for transporting analytes through a chromatographic column has materialized only recently. See, for example, Dittman et al. (1996) *J. Chromatogr. A* 744:6374; Cikalo et al. (1998) *Analyst* 123:87R–102R; and Majors (1998) *LC-GC* 16:96–100. Capillary electrochromatography (CEC) continues to develop rapidly and find applications in a variety of areas, including the separations of enantiomers. See Wistuba, D.; Schurig, V. *J.Chromatogr.* (2000) 875: 255–276 and references cited therein. Several groups have adapted an HPLC-like bead approach to a capillary column format in an attempt to achieve the high efficiencies predicted by theory. Although packed capillaries are currently the most common column technology, this approach is accompanied by several difficulties. For example, the surface charge often results only from residual surface silanols, making effective control of the magnitude and direction of EOF poor. Additionally, column packing procedures are often tedious, requiring in situ frit fabrication. These frits may have limited stability and/or permeability, and their heterogeneities may initiate spontaneous outgassing and bubble formation. These problems have led to the development of new column technologies—open-tubular and monolithic columns—that eliminate many of the drawbacks of packed capillary columns.

In open-tubular electrochromatography (OT-EC), the stationary phase is covalently attached, coated, or adsorbed onto the inner capillary wall. See Tsuda et al. (1982) *J. Chromatogr.* 248:241–247; Guo et al. (1995) *Anal. Chem.* 67:2511–2516; and Sawada et al. (1999) *Electrophoresis* 20:24–30. Since the surface of the open tube is very limited, these columns only afford a low sample capacity. Selective etching of the wall may be used to increase the overall surface area and improve the loadability (Pesek (2000) *J. Chromatogr. A* 887:31–42). In contrast, monolithic stationary phases often possess much higher surface areas and adsorption capacities. To date, several different approaches to monolithic CEC columns have been reported. Siliceous monoliths for CEC have been prepared by polycondensation of alkoxysilanes using a sol-gel process within the capillary tubing followed by post-functionalization, as reported by Tanaka et al. (2000) *J. High Resol. Chromatogr.* 23:111–116. In order to minimize the risk of shrinkage typical of sol-gel transitions that can lead to cracks in the bed, the overall volume of the inorganic matrix has been reduced by filling the column with traditional chromatographic particles prior to initiating the sol-gel process (Dulay et al. (1998) *Anal. Chem.* 70:5103–5107; Tang et al. (1999) *J. Chromatogr. A* 837:35–50; Chirica et al. (1999) *Electrophoresis* 20:50–56; Ratnayake et al. (2000) *J. High Resol. Chromatogr.* 23:81–88). Consolidation of a packed bed by sintering the particles has also been proposed as a method for the preparation of monolithic columns (see Dittman et al. (1997) *J. Capil. Electrophoresis* 4:201–212 and Asiaie et al. (1998) *J. Chromatogr. A* 806:251–263) but this technique is even more laborious and the surface chemistry of the stationary phase is often destroyed during the sintering process necessitating post-functionalization. As described by Svec et al. (2000) *J. High Resol. Chromatogr.* 23:3–18 and Svec et al. (2000) *J. Chromatogr. A*, 887:3–30, functional monomers have been polymerized in situ within bare or vinylized fused silica tubing in the presence of pore forming solvents to yield continuous porous crosslinked organic polymers. Examples of this approach include polyacrylamide-based gels (Liao et al. (1996) *Anal. Chem.* 68:3468–3472; Ericson et al. (1999) *Anal. Chem.* 71:1621–1627; Hjertén (1999) *Ind. Eng. Chem. Res.* 38:1205–1214; Fujimoto et al. (1995) *J. Chromatogr. A* 716:107–113; Fujimoto et al. (1996) *Anal. Chem.* 68:2753–2757) polyacrylamide copolymers prepared in the presence of poly(ethylene glycol) (Palm et al. (1997) *Anal. Chem.* 69:4499–4507) molecularly imprinted "superporous" monoliths (Schweitz et al. (1997) *Anal. Chem.* 69:1179–1183; Nilsson et al. (1994) *J. Chromatogr. A* 680:57–61; Schweitz et al. (1998) *J. Chromatogr. A* 817:5–13), highly crosslinked polystyrene (Gusev et al. (1999) *J. Chromatogr. A* 855:273–290; Xiong et al. (2000) *J. High Resol. Chromatogr.* 23:67–72) and polymethacrylate matrices (Peters et al. (1997) *Anal. Chem.* 69:3646–3649; Peters et al. (1998) *Anal. Chem.* 70:2288–2295; Peters et al. (1998) *Anal. Chem.* 70:2296–2302).

However, only a very limited number of studies have attempted the use of monolith technology for enantiomeric separations. These include Schweitz et al. (1997), supra, Peters et al. (1998) *Anal. Commun.* 35:83–86, supra, Nilsson et al. (1994), supra, Koide et al. (1999) *Anal. Sci.* 15:791–794, and Koide et al. (2000) *J. High Resol. Chromatogr.* 23:59–66. Peters et al. (1998) is a representative reference, and describes an enantiomeric separation medium prepared by copolymerization of multiple monomers including an ionic monomer (2-acrylamido-2-methyl-1-propane sulfonic acid), a chiral monomer, a crosslinking monomer, and a functional monomer. It has been found, however, that using separate ionic and chiral monomers does not allow one to achieve a high content of both monomers in the separation medium simultaneously. In particular, ionic monomers often have poor solubility in the polymerization mixture.

Thus, Peters et al. (1998) and other prior methods proposed for preparing monolithic materials suitable for enantiomeric separations have suffered from several drawbacks. Primarily, no one monolithic material is capable of performing a variety of separate functions, e.g., the ability to carry charge, the ability to consistently and specifically attract a single enantiomer from a racemic mixture, the ability to facilitate electroosmotic flow (i.e., to act as an electroosmotic pump), and the ability to substantially reduce (or "shield") undesired electroosmotic flow (EOF) along the interior wall of a column or channel. In addition, Peters et al. teach the use of ionic (or "pre-ionized") monomers to incorporate charge into monoliths. This reduces the versatility of the method as few such monomers exist and those available are often poorly soluble in a largely organic medium, and the high reactivity of the ionic monomer may have a deleterious effect on polymerization.

There is accordingly a need in the art for a monolithic material that is effective in enantiomeric separation and simultaneously provides a variety of functions, namely: (1) acts, as a chromatographic packing material; (2) provides a continuous tortuous path and a large interacting surface for a flowing liquid; (3) performs specific chiral recognition; (4) acts as a charge carrier; (5) acts as an electroosmotic pump; and (6) acts as a surface coating along a column or channel wall. The present invention now provides methods, materials and separation devices that simultaneously fulfill all of the aforementioned requirements. The novel monolithic material has ionizable functionalities as well as multiple interaction sites located within a rigid molecular framework, the interactions sites containing both stereogenic centers and bulky groups to form series of favorable binding "pockets". The chiral species within the monolithic material provide the surface charges required to generate EOF and therefore eliminate the need for the addition of a charged comonomer, and affords the required stereoselective interactions with complementary chiral analytes, resulting in the separation of enantiomers. Furthermore, capillaries, columns and channels suitable for effecting enantiomeric separations may be readily prepared in a simple and straightforward manner using a simple molding process and in situ polymerization so as to avoid the fabrication of frits and the packing of small beads into capillaries.

SUMMARY OF THE INVENTION

Accordingly, it is a primary object of the invention to provide a device for use in conducting chiral electrochromatography using an enantioselective separation medium that overcomes the aforementioned drawbacks in the art.

It is another object of the invention to provide such a device in the form of a capillary tube, microchannel, or the like, i.e., a device that comprises an electrochromatographic conduit containing an enantioselective separation medium of the invention.

It is still another object of the invention to provide such a device wherein the enantioselective separation medium is a monolithic, ionizable copolymer that acts as a continuous separation medium and contains pendant chiral selector groups.

It is yet another object of the invention to provide such a device wherein the enantioselective separation medium is a porous organic polymer.

It is an additional object of the invention to provide a method for making the aforementioned device.

It is a further object of the invention to provide an enantioselective separation medium for use in the aforementioned device.

It is still a further object of the invention to provide a method for making an enantioselective separation medium for use in the electrochromatographic devices of the invention.

Additional objects, advantages and novel features of the invention will be set forth in part in the description which follows, and in part will become apparent to those skilled in the art upon examination of the following, or may be learned by practice of the invention.

In one embodiment of the invention, then, a device is provided for use in chiral electrochromatography, wherein the device comprises an electrochromatographic conduit containing an enantioselective separation medium comprised of a monolithic, ionizable copolymer that acts as a continuous separation medium and contains pendant chiral selector groups. Because the monolithic copolymer is ionizable and contains stereogenic centers (i.e., in the pendant chiral selector groups), once the separation medium is ionized it acts as charge carrier as well as chiral selector. The electrochromatographic device may comprise a capillary tube containing an enantioselective separation medium of the invention, or the device may be a microfluidics separation device wherein the enantioselective separation medium is contained in one or more "microchannels" within the device.

In another embodiment of the invention, an enantioselective separation medium is provided that comprises a chiral copolymer prepared by copolymerization of a mixture comprising (a) an ionizable chiral monomer, (b) a crosslinking comonomer, (c) a polymerization initiator, (d) a porogenic solvent, and optionally (e) a functionalized monovinyl comonomer. In preferred embodiments, the functionalized monovinyl comonomer is employed; typically, the functionalized monovinyl comonomer contains a hydrophilic moiety (e.g., a hydroxyl group) or a precursor to a hydrophilic moiety (e.g., an epoxy group).

In a related embodiment of the invention, an enantioselective separation medium is provided that comprises a chiral copolymer prepared by copolymerization of a mixture comprising (a) a chiral monomer; (b) a crosslinking comonomer, (c) a polymerization initiator, (d) a porogenic solvent, (e) an ionizable comonomer or a precursor thereto, and optionally (f) a functionalized monovinyl comonomer. In preferred embodiments, the functionalized monovinyl comonomer is employed, as above.

In other embodiments of the invention, methods are provided for preparing the aforementioned enantioselective separation medium and electrochromatographic separation device, the methods involving copolymerization of a polymerization mixture comprising (a) an ionizable chiral monomer, (b) a crosslinking comonomer, (c) a polymerization initiator, (d) a porogenic solvent, and optionally (e) a functionalized monovinyl comonomer. In a related embodiment, a separate ionizable comonomer is incorporated into the polymerization mixture, in which case the chiral monomer may or may not be ionizable. Again, in preferred embodiments, the functionalized monovinyl comonomer is employed. Polymerization may be thermally initiated or initiated using radiation, typically ultraviolet (UV) radiation.

DETAILED DESCRIPTION OF THE INVENTION

Definitions and Overview

Figure 1:
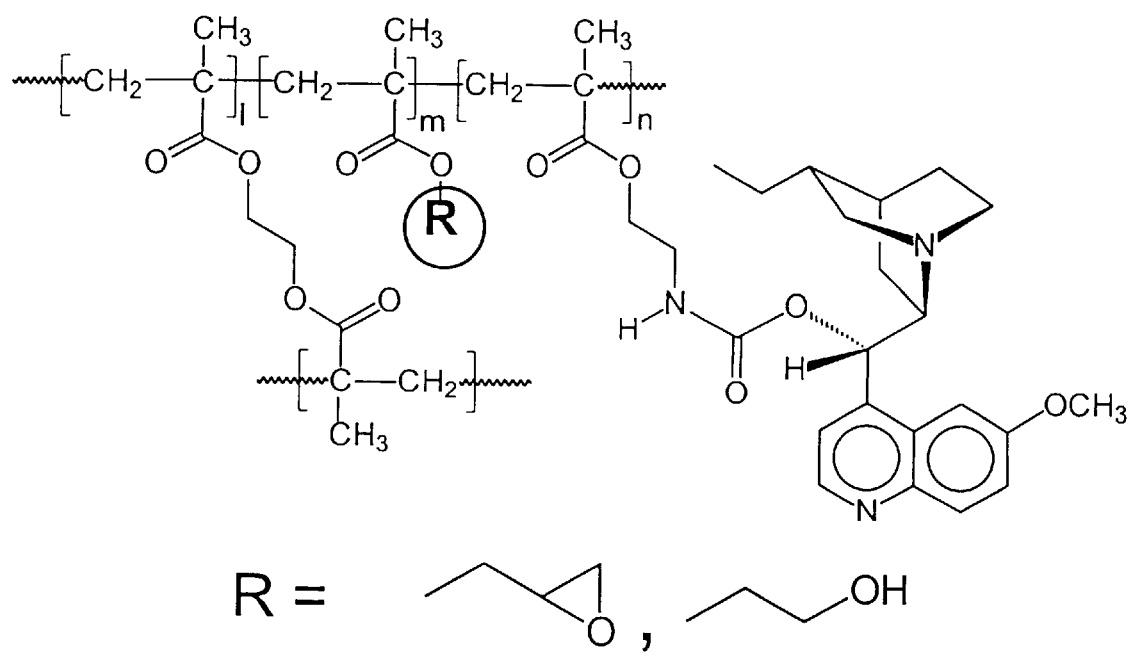
FIG. 1 is a representation of the chemical structure of the chiral monolithic polymer prepared by copolymerization of O-[2-(methacryloyloxy)ethylcarbamoyl]-10,11-dihydroquinidine (1), as described in Example 2.

Before describing the present invention in detail, it is to be understood that unless otherwise indicated this invention is not limited to specific monomers, copolymers or electrochromatographic devices, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a monomer" refers to one monomer or to a combination of monomers, reference to "a copolymer" refers to one copolymer or to a combination of copolymers, reference to "a microchannel" refers to one microchannel or a plurality of microchannels, and the like.

In describing and claiming the present invention, the following terminology will be used in accordance with the definitions set out below.

The term "monolithic" refers to a separation medium in the form of a single continuous piece of a porous material completely filling the desired space of an electrochromatographic device, i.e., a capillary interior, a microchannel, or the like.

The terms "chiral separation" and "enantioselective separation" refer to a process leading to the-separation of a mixture of enantiomers into two fractions, each containing one enantiomer in excess.

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optional third comonomer" means that a third comonomer may or may not be present and that the description includes both such instances.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, 2-ethylhexyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four-carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms.

The term "aryl" as used herein, and unless otherwise specified, refers to a univalent aromatic substituent containing a single aromatic ring or multiple aromatic rings that are fused together or linked covalently.

The term "heteroatom-containing" refers to a molecule or molecular fragment in which one or more carbon atoms is replaced with an atom other than carbon, e.g., nitrogen, oxygen, sulfur, phosphorus or silicon.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. By way of example, substituted hydrocarbyl groups include hydroxyalkyl and hydroxyalkenyl groups.

By "substituted" as in "substituted dihydropyrimidine," "substituted cycloalkane," and the like, is meant that in the dihydropyrimidine, cycloalkane or other moiety, at least one hydrogen atom bound to a carbon atom is replaced with one or more substituents that are functional groups such as amino, halo, hydroxy, etc.

The term "ionizable" refers to a group that is electronically neutral at a specific pH, but can be ionized and thus rendered positively or negatively charged at higher or lower pH, respectively, or as a result of one or more chemical reactions. The "ionizable" moieties of the invention are moieties that are capable of being rendered either positively or negatively charged. By way of example, such groups include amines, mono-substituted amines, di-substituted amines, nitrogen-containing heterocycles, carboxylic acids, and the like. In the context of the present invention, the "ionizable" chiral monomer and the "ionizable" comonomer, if used, refer to monomers that are electronically neutral when incorporated into the polymerization mixture, but which, following copolymerization and preparation of the monolith, are readily ionized at higher or lower pH and/or upon chemical reaction. Thus, the "ionizable" moieties are in fact ionized during the enantioselective separation process.

The term "ionic" refers to a group that is ionized or exists in the form of a salt (i.e., is associated with a counterion). The "ionizable" chiral monomer and the "ionizable" comonomer used herein are not "ionic" under the conditions used for copolymerization.

The Enantioselective Separation Medium

The invention is thus directed to a novel enantioselective separation medium and to electrochromatographic devices for enantioselective separation of racemic compounds that employ the novel separation medium. The separation medium is comprised of a monolithic polymeric material that is capable of acting as a continuous separation medium in an electrochromatographic capillary, column, microchannel or the like, and incorporates chiral monomer units capable of ionization, or, in an alternative embodiment, incorporates a combination of chiral and ionizable monomers. The monolithic polymer thus contains functionalities that are ionized upon a change in pH or by chemical modification. In addition, upon application of an electric field, undesired EOF at the interior wall of a silica capillary or the like is shielded, either by neutralization of surface silanol groups by positively charged groups on the adjacent monolith or by the bulk or charges of the ionized monolith itself. A similar effect is obtained with a positively charged surface when there are negatively charged groups in the monolith.

The copolymer that serves as the aforementioned chiral separation medium is preferably prepared by copolymerization of at least two types of monomers, a chiral monomer that is an addition polymerizable ionizable monomer with a pendant chiral selector moiety, and a crosslinking comonomer, typically a polyvinyl comonomer, which enables crosslinking of the copolymer as it is synthesized. An optional third comonomer is a functional monovinyl comonomer, i.e., a monovinyl comonomer containing a functional group, preferably a hydrophilic group such as a hydroxyl moiety. Alternatively, the copolymer is prepared by copolymerization of an addition polymerizable chiral monomer that has a pendant chiral selector moiety (and may or may not be an ionizable monomer), an ionizable comonomer, a crosslinking comonomer such as a polyvinyl comonomer, and optionally a functional monovinyl comonomer as described above with respect to the preferred embodiment.

In a preferred embodiment, then, the chiral monomer units are capable of ionization, and additional ionizable monomers are not used. Preferably, the chiral monomer units are not only capable of performing chiral separation and carrying charge, but also inherently facilitate the desired flow of liquid, i.e., are capable of electroosmotic pumping. As will be discussed in detail below, the monolithic polymer containing the chiral monomer units is readily tailored to achieve a wide range of porosity parameters, i.e., pore size, pore size distribution, and overall pore volume.

More specifically, the chiral comonomer, which comprises an addition polymerizable monomer with a pendant chiral selector moiety, is generally a vinyl monomer that undergoes vinyl polymerization, and preferably is an acrylate or methacrylate monomer. The chiral monomer and/or the optional ionizable comonomer contain ionizable moieties that are rendered charged, preferably although not necessarily positively charged, upon application of an electrical potential. Examples of such ionizable moieties include, but are not limited to: nitrogen-containing moieties such as amino groups, mono-substituted amino groups (i.e., —NHR groups wherein R is typically hydrocarbyl, substituted hydrocarbyl, heteroatom-containing hydrocarbyl or substituted heteroatom-containing hydrocarbyl), di-substituted amino groups (i.e., —NR$_2$ groups), nitrogen-containing heterocycles, etc.; and acidic groups such as carboxylic acid groups. When an ionizable chiral monomer is employed, the ionizable moieties may or may not be present within the pendant chiral selector moiety.

The chiral selector moiety of the chiral monomer should contain one or more stereogenic centers that act as binding pockets for a particular enantiomer. Examples of such pendant chiral selectors include, but are not limited to:

cinchona alkaloids typically used in enantiomeric separations, including quinine, epi-quinine, quinidine, epi-quinidine, cinchonine, epi-cinchonine, cinchonidine, epi-cinchonidine, 10,11-dihydroquinine, 10,11-dihydro-epi-quinine, 10,11-dihydro-quinidine, 10,11-dihydro-epi-quinidine, 10,11-dihydro-cinchonine, 10,11-dihydro-epi-cinchonine, 10,11-dihydro-cinchonidine, 10,11-dihydro-epi-cinchonidine, and analogs of any of the foregoing;

dihydropyrimidines substituted with one or more moieties, preferably moieties that are ionizable to give a positive charge, e.g., amino, alkylamino, dialkylamino and nitrogen-containing cyclic moieties, wherein such dihydropyrimidines include 4-substituted dihydropyrimidines, 1,4-disubstituted dihydropyrimidines, 4-substituted, 2-thio-dihydropyrimidines, and 1,4-disubstituted, 2-thio-dihydropyrimidines, wherein suitable substituents include, but are not limited to, 4-amino, 1,4-diamino, 4-aminophenyl, 2-methyl-4-aminophenyl, 4-dimethylaminophenyl, 2-methoxy-4-aminophenyl, 2-hydroxy-4-aminophenyl, (other suitable substituents for dihydropyrimidines useful as the pendant chiral selector moiety herein may be readily deduced by those skilled in the art and/or are described in the pertinent texts and literature, e.g., in Lewandowski et al. (1999) *J. Comb. Chem.* 1:105–112);

1,2-disubstituted aliphatic cycloalkanes, particularly 1,2-disubstituted cyclopentanes and 1,2-disubstituted cyclohexanes, most preferably 1,2-disubstituted cyclohexanes, wherein suitable substituents may be the same or different and are as described above with respect to substituted dihydropyrimidines, with preferable substituents again being nitrogen-containing moieties such as amino groups, alkylamino groups, dialkylamino groups, and nitrogen-containing cyclic groups;

chiral amino acids and derivatives thereof, e.g., L-valine, L-phenylalanine and L-proline, and amide linked derivatives of such amino acids formed with amines, preferably although not necessarily aromatic amines such as 3,4,5-trimethoxyaniline, 3,5-dimethylaniline, 3-benzyloxyaniline, 5-aminoindane, 4-t-butylaniline, 4-biphenylamine, 1-aminonaphthalene, 4-tritylaniline, 2-aminoanthracene, 2-aminofluorene, 2-aminoanthraquinone, and 3-amino-1-phenyl-2-pyrazolin-5-one (again other chiral amino acids and derivatives thereof may be readily deduced by those skilled in the art and/or are described in the pertinent texts and literature, e.g., in Murer et al. (1999) *Anal. Chem.* 7:1278–1284); and chiral monomers derived from monosaccharides, disaccharides, oligosaccharides, and polysaccharides such as monoacryloylated and monomethacryloylated glucose, saccharose, and α-, β-, and γ-cyclodextrins.

Preferred chiral monomers are the cinchona alkaloids, with 10,11-dihydroquinidine derivatives representing exemplary such monomers. Optimal chiral monomers having pendant 10,11-dihydroquinidine derivatives are monomethacrylate-functionalized 10,11-dihydroquinidine derivatives having the structure of formula (I)

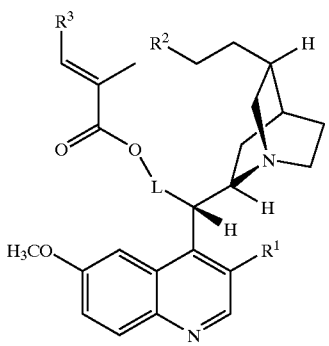

(I)

wherein:
- $R^1$ is H, hydroxyl, or alkoxy (typically lower alkoxy);
- $R^2$ is H, alkyl (typically lower alkyl) or aryl;
- $R^3$ is H or methyl; and
- L is a linking group that does not interfere with retention of a chiral moiety, and wherein suitable L groups include, for example, carbamate linkages, alkylene carbamate linkages, carbonate linkages, alkylene carbonate linkages, and the like.

A specific such monomer is O-[2-methacryloyloxy) ethylcarbamoyl]-10,11-dihydroquinidine, having the structure of formula (II)

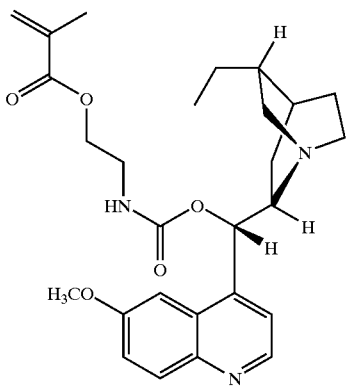

(II)

When a separate ionizable comonomer is employed, in which case the chiral monomer may or may not contain ionizable sites, the chiral monomer is preferably an acrylate, methacrylate, acrylamide or methacrylamide containing a pendant chiral selector moiety such as a sugar or amino acid derivative, a chiral amine, a chiral alcohol, or a chiral thiol. The ionizable monomer is preferably an acrylic acid or methacrylic acid monomer containing an amino group, 2-vinylpyridine, 4-vinylpyridine or a carboxylic acid group. Tertiary amino groups are preferred. Examples of such ionizable monomers include, but are not limited to, 2-(dialkylaminoethyl) acrylate or methacrylate, 2-morpholinoethyl acrylate or methacrylate, acrylic or methacrylic acid, itaconic acid, N-methacryloyl and N-acryloyl amino acids, and the like. The ionizable monomer may also be a reactive monomer such as glycidyl methacrylate or acrylate, i.e., a monomer that becomes ionizable upon reaction with another compound such as an amine or an amino acid.

The second comonomer, as noted above, is preferably a polyvinyl comonomer that enables crosslinking of the copolymer as it is synthesized. Suitable polyvinyl comonomers include, but are not limited to, alkylene bis-acrylamides, alkylene bis-methacrylamides, alkylene diacrylates, alkylene dimethacrylates, hydroxyalkylene diacrylates and hydroxyalkylene dimethacrylates where the alkylene chain is comprised of 1 to about 6 carbon atoms, oligoethylene glycol diacrylates and oligoethylene glycol dimethacrylates in which the oligoethylene glycol moiety is comprised of 2 to about 12 oxyethylene units, acryloylated and methacryloylated polyols, pentaerythritol di-, tri- and tetraacrylate, glycerol dimethacrylate, sugars (e.g., monosaccharides and disaccharides) functionalized with multiple vinyl and/or allyl groups, and mixtures of any such polyvinyl comonomers. Specific and preferred polyvinyl comonomers include ethylene dimethacrylate (EDMA), trimethylolpropane triacrylate, triethylene glycol dimethacrylate, and pentaerythritol tetraacrylate.

The optional third comonomer is a monovinyl comonomer that serves as a "spacer," allowing the fraction of the chiral monomer in the copolymer to be controlled. That is, by incorporating a third comonomer into the copolymer at a predetermined chiral monomer/third comonomer ratio, the degree of functionalization (i.e., functionalization of the copolymer introduced by virtue of the chiral monomers) can be controlled. The chiral monomers, as noted above, are positively charged under electrochromatographic conditions, and the positively charged sites both generate the desired EOF and provide for chiral discrimination. The monovinyl comonomer has a functional group, preferably a hydrophilic group such as a hydroxyl group, or a precursor to a hydrophilic group such as an epoxy group (e.g., in glycidyl methacrylate). The monovinyl comonomer, by virtue of its polarity, also controls the polarity of the pore surface after preparation of the porous monolithic copolymer. Suitable monovinyl comonomers include, without limitation, hydroxyalkyl acrylates and methacrylates such as 2-hydroxyethyl acrylate, 2-hydroxyethyl methacrylate, 3-hydroxypropyl acrylate, 3-hydroxypropyl methacrylate, glycidyl acrylate, glycidyl methacrylate, oligoethylene glycol monoacrylates and oligoethylene glycol methacrylates in which the oligoethylene glycol moiety is comprised of 2 to about 12 oxyethylene units, and monovinylized sugars, typically monosaccharides or disaccharides. If glycidyl acrylate or glycidyl methacrylate is used as the third comonomer, its resulting epoxide functionality, which is a precursor of a diol group, may be subjected to a ring-opening reaction to give a hydrophilic hydroxyalkyl group, or may be used to further functionalize the copolymer, e.g., to modify the chiral recognition sites or introduce an ionizable functionality, for example by reaction with an amine. The crosslinking comonomer or the crosslinking comonomer plus the optional monovinyl comonomer are generally present in the polymerization mixture in an amount of from about 10 to 80, more preferably in an amount of from about 30 to 60% by weight. As the amount of crosslinking comonomer controls to a large extent the degree of crosslinking of the copolymer, and crosslinking in turn impacts on porosity, the amount of crosslinking comonomer should be selected to provide the desired porosity profile (see Example 7).

The process used to prepare the chiral monolithic material comprised of the aforementioned copolymer will begin by preparing a polymerization mixture. A suitable polymerization mixture is one which contains at least the chiral monomer and the crosslinking comonomer (and generally the hydrophilic monovinyl comonomer as well), a polymerization initiator and a porogenic solvent. If a separate ionizable comonomer is used, it is incorporated into the polymerization mixture as well.

The polymerization initiator used may be any conventional free radical-generating polymerization initiator. Examples of suitable initiators include peroxides such as OO-t-amyl-O-(2ethylhexyl)monoperoxycarbonate, dipropylperoxydicarbonate, and benzoyl peroxide, as well as azo compounds such as azobisisobutyronitrile, 2,2'-azobis(2-amidino-propane)dihydrochloride, and 2,2'-azobis(isobutyramide)dihydrate. The initiator is generally present in the polymerization mixture in an amount of from about 0.2 to 5% by weight of the monomers. With photopolyrherization, photosensitizers such as benzoin, benzophenone, benzil, fluorene, pyrene-triethylamine, methylene blue-p-toluenesulfinate, etc., may also be incorporated into the polymerization mixture.

The porogenic solvent (or "porogen") used enables control over the pore size of the monolithic copolymer independently of the composition of the polymerization mixture. The porogenic solvent may be selected from a variety of different types of materials, provided that the solvent is a liquid at the polymerization temperature employed and serves to dissolve all components of the polymerization mixture. For example, suitable porogenic solvents include water, alcohols (particularly alcohols and diols having 2 to about 18 carbon atoms), low molecular weight polyethylene glycols (i.e., polyethylene glycols that, again, are liquid at the polymerization temperature used), low molecular weight block copolymers of ethylene oxide and propylene oxide, aliphatic hydrocarbons, aromatic hydrocarbons, esters (including carboxylic acid esters, e.g., ethyl hexyl acetate and other alkyl acetates), nitrites (including nitriles of carboxylic acids, e.g., acetonitrile), ketones, ethers and mixtures thereof. A particularly preferred porogenic solvent comprises a mixture of cyclohexanol and 1-dodecanol, as described in the examples herein. The porogenic solvent is generally present in the polymerization mixture in an amount of from about 20 to 90, more preferably in an amount of from about 40 to 70% by weight.

Prior to polymerization, the mixture is preferably deaerated by conventional means such as bubbling an inert gas such as nitrogen through the mixture for a sufficient period of time to remove oxygen present in the mixture. Once the polymerization mixture is prepared and deaerated, it is generally introduced into a capillary, column, microchannel or the like, as will be discussed in further detail below. Once the polymerization mixture is in place, polymerization is carried out in a conventional manner, using heat or radiation, with thermal polymerization preferred as enantioselectivity of the copolymeric product tends to be somehow higher. With a thermal polymerization, the reaction is generally carried out at a temperature of from about 50° C. to about 90° C. for a period of from about 6 to 24 hours, depending on the initiator and monomers used. The polymerization is preferably carried out in an inert atmosphere such as nitrogen or argon. While heating may be supplied by any means known in the art, it is presently preferred to immerse a sealed capillary or column containing the polymerization mixture into a heated bath. If radiation is used to initiate polymerization, the reaction may be conducted at ambient temperature using conventional ultraviolet lamps or lasers and a reaction time sufficient to ensure that polymerization is complete; generally, this is on the order of 1–20 hours.

After polymerization is complete, the pores of the monolithic medium are washed to remove any remaining porogenic solvent. Suitable washing solvents include water, methanol, ethanol, benzene, toluene, acetone, tetrahydrofuran, diethylether, and dioxan. This washing process may be done in stages; for example, by washing with a solvent, then with water and then a solvent again, or by continuous washing with a solvent. The washing step is preferably carried out by pumping the solvent through the capillary, column or channel filled with the monolithic copolymer.

It should be noted that a number of variables in the polymerization process are available for controlling the porosity profile of the monolithic copolymer that is synthesized. The variables include the percentage of crosslinking comonomer, as noted above, as well as the percentage of the monovinyl comonomer (if used), the reaction temperature, concentration of polymerization initiator, and composition and amount of the porogenic solvent.

Prior to use in a chiral electrochromatographic process, the monolithic copolymer is ionized, either by washing with a suitable buffer solution, or through one or more chemical modification steps such as a quaternization reaction or the opening of an epoxide with an amine, followed by washing with an acidic buffer. After the washing step, the monolithic copolymer is ready for use in a chiral electrochromatographic separation process.

Use in Enantiomeric Separation Devices

Electrochromatographic processes using relatively small sample volumes are frequently carried out in a chamber or column of capillary dimensions, e.g., in a capillary tube. Capillary electrochromatography involve moving a sample through a capillary packed with a separation medium under the influence of an applied electric field. Depending on the nature of the sample (i.e., whether or not the sample carries an electric charge) as well as on the surface chemistry of the separation medium, the sample may be moved through the separation medium under the direct influence of the applied electric field or as a result of bulk fluid flow through the pathway resulting from the application of the electric field, i.e., electroosmotic flow.

The capillary tubes useful in conjunction with the present invention may be any conventional capillary tube, preferably, for convenience, one that is readily available commercially. Such capillary tubes are generally comprised of fused silica or plastic. The dimensions of the tube are not critical, but the tube will generally have an inner diameter in the range of about 0.02 to about 0.8 mm and a length in the range of from about 50 to 1000 mm, more usually in the range of from about 100 to 400 mm. Capillary tubes coated at the outer surface are available and may be advantageously employed in conjunction with the present invention. For example, polyimide-coated capillary tubes are particularly suited to in situ preparation of monoliths using a thermal polymerization process, while capillary tubes coated with a fluorinated hydrocarbon polymer are particularly suited to in situ preparation of monoliths using radiation-initiated polymerization.

In another embodiment of the invention, then, a single capillary tube or a plurality of capillary tubes used in parallel are provided that are useful in conducting an enantiomeric separation of a mixture of enantiomers, each tube containing as an enantioselective separation medium a chiral, monolithic, ionizable copolymer as described in the preceding section.

Enantiomeric separation using the novel chiral separation medium may also be conducted in a microfluidic separation device. Such microfluidic separation devices, as known in the art, contain at least one "microchannel" comprised of a conduit that serves as an electrochromatographic flow path, having a cross-sectional area that provides for flow of liquid through the device. The microchannel may have any of a variety of configurations, including tubular, trench-like or other convenient configuration, where the cross-sectional shape of the microchannel may be circular, ellipsoidal, square, rectangular, triangular, or the like. The cross-sectional diameter (or width or height, depending on cross-sectional shape) will generally be at least about 1 μm, usually at least about 10 μm, but will not exceed about 200 μm, and will usually not exceed about 100 μm. Depending on the nature of the device, the microchannel may be straight, curved, or have another convenient configuration. The microchannel is etched or otherwise formed in a suitable substrate, typically fabricated from glass, fused silica, plastics (e.g., polymethyl methacrylate, polycarbonate, polyethylene terephthalate, polystyrene, polyimide, poly(dimethylsiloxane), polypropylene or other polyolefin, etc.), or the like. In order to serve as an electrochromatographic conduit, the microchannel must be associated with a means for introducing fluid, at one terminus, and a means for extracting fluid, at a second terminus. Also, the microchannel must have associated with it at least one pair of electrodes for applying an electric field to the separation medium in the microchannel, with, typically, one electrode present at each terminus of the microchannel. The device may be fabricated using any convenient means, including conventional molding, casting, embossing, and etching techniques. Generally, one or more microchannels are formed in a planar support plate, and a cover plate is then placed over and sealed to the support plate.

In another embodiment of the invention, then, such a microfluidic separation device is provided in which one or more microchannels contain the novel chiral monolithic material as the enantiomeric separation medium. Preferably, each microchannel is provided with the separation medium by copolymerization the chiral monomer, the crosslinking comonomer, and optionally the hydrophilic monovinyl comonomer, in situ, so that a "packing" step as is traditionally required is unnecessary.

Accordingly, the invention represents an important advance in the art insofar as a monolithic enantioselective separation medium is now provided that not only provides chiral recognition and separation of enantiomers, but also serves as a charge carrier and an electroosmotic pump. The enantioselective separation medium can be prepared in a single step, by copolymerization in situ, to give the desired material in high yield. The monolith tightly fills the capillary or microchannel used as a mold.

In a preferred embodiment, the monolith contains ionizable functionalities that are basic, i.e., functionalities that are ionized, during a separation process, such that they have a positive charge. These ionizable groups provide for stronger adhesion to the walls of the capillary or microchannel due to the Coulombic interaction that occurs between the basic groups of the monolith and the acidic surface silanol groups of fused silica or glass substrates. Therefore, when a basic monolith is used in conjunction with a fused silica or glass surface, no pretreatment of the capillary or microchannel is necessary as is required with conventional separation devices (typically, fused silica capillaries or glass chips have had to be treated with a functionalized silane such as 3-(methacryloyloxypropyl)-trimethoxysilane) in order to achieve the required adhesion of the separation medium). The strong Coulombic interaction between the basic groups of the monolith and acidic surface silanol groups also neutralizes the surface silanol groups, which would otherwise give rise to electroosmotic flow toward the cathode (cathodic flow). This direction would be opposite to the anodic flow supported by the basic functionalities of the monolith. Accordingly, a basic monolithic separation medium of the invention also eliminates this cathodic flow, resulting in far more efficient electrochromatographic separation devices. When the monolith contains ionizable acidic functionalities, e.g., ionizable carboxylic acid groups, the large number of functionalities of the monolith effectively shields the surface of the capillary or microchannel, thus reducing undesired wall effects.

Finally, the novel separation medium is stable at elevated temperatures (up to at least about 200° C.) and withstands the high pressures typically used in electrochromatographic separation processes.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the materials of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in degrees C. and pressure is at or near atmospheric.

EXAMPLE 1

Preparation of O-[2-(methacryloyloxy)ethylcarbamoyl]-10,11-dihydroquinidine (1)

10,11-dihydroquinidine (Fluka, Buchs, Switzerland)] and 2 isocyanatoethyl methacrylate [Dow Chemical Co., Midland, Mich.] (1.1 molar excess) were dissolved in sufficient dry THF to completely dissolve the reagents. Three drops of a dibutyltin dilaurate catalyst solution and 100 μL of a 4-methoxyphenol (Aldrich, Milwaukee, Wis.) (1 mg/mL in dry THF) inhibitor solution was added to the dissolved 10,11-dihydroquinidine and 2-isocyanatoethyl methacrylate in THF. The reaction mixture was then stirred overnight at room temperature. The THF solvent was evaporated and the residue purified by flash chromatography on silica using a chloroform/methanol mixture as the eluent. The product was recrystrallized from a dichloromethane petrolether mixture. Physical properties: m.p.: 109–111° C.; $[\alpha]^{23}_{Na589}$=+62.0, $[\alpha]^{23}_{Hg578}$=+65.2, $[\alpha]^{23}_{Hg546}$=+73.7 c=0.988; MeOH); IR (KBr): 3420, 3200, 2920, 2870, 1715, 1620, 1570, 1530, 1500 cm$^{-1}$. $^1$H NMR (CDCl$_3$): 0.93 (t, 3H), 1.2–1.85 (m, 8H), 1.90 (s, 3H), 2.55–2.95 (m, 4H), 3.24 (m, 1H), 3.50 (m, 2H), 3.98 (s, 3H), 4.2 (t, 2H), 5.10 (s, 1H), 5.50 (s, 1H), 6.03 (s, 1H), 6.48 (d, 1H), 7.36 (m, 2H), 7.46 (d, 1H), 8.00 (d, 1H), 8.75 (d, 1H) ppm.

EXAMPLE 2

Preparation of Monolithic Capillary Columns

Monolithic capillary columns for the practice of the invention were prepared by in situ free radical copolymerization of the quinidine-based chiral monomer, O-[2-methacryloyloxy)ethylcarbamoyl]-10,11-dihydroquinidine (1), prepared according to the method of Example 1. The free radical initiator azobisisobutyronitrile (AIBN, 1 wt % with respect to the monomers, obtained from Aldrich) was added to a polymerization mixture consisting of 40 wt % monomers and 60 wt % of a porogenic solvent mixture of 1-dodecanol and cyclohexanol. The polymerization mixture contains three monomers: O-[2-methacryloyloxy)ethylcarbamoyl]-10,11-dihydroquinidine (Example 1), a comonomer, either glycidyl methacrylate (GMA, obtained from Kodak, Rochester, N.Y.) or 2-hydroxyethyl methacrylate (HEMA, obtained from Sartomer, West Chester), and a crosslinker, ethylene dimethacrylate (EDMA) in proportions as specified in Table 1.

TABLE 1

| composition | wt. % 1 (wt. % total monomers) | HEMA or GMA, wt. % (wt. % total monomers) | EDMA, wt. % (wt. % total monomers) | dodecanol wt. % (wt. % total solvent) | cyclohexanol wt. % (wt. % total solvent) |
|---|---|---|---|---|---|
| Ia) i | 4(10) | 20(50) | 16(40) | 20(33) | 40(67) |
| Ia) ii | 4(10) | 20(50) | 16(40) | 35(58) | 25(42) |
| Ia) iii | 8(20) | 16(40) | 16(40) | 35(58) | 25(42) |
| Ia) iv | 12(30) | 12(30) | 16(40) | 35(58) | 25(42) |
| Ia) v | 4(10) | 20(50) | 16(40) | 5(8) | 55(97) |
| Ia) vi | 4(10) | 20(50) | 16(40) | 10(17) | 50(83) |
| Ia) vii | 4(10) | 20(50) | 16(40) | 15(25) | 45(75) |
| Ia) viii | 4(10) | 20(50) | 16(40) | 25(42) | 35(58) |
| Ia) ix | 4(10) | 20(50) | 16(40) | 30(50) | 30(50) |
| Ia) x | 4(10) | 20(50) | 16(40) | 40(67) | 20(33) |
| Ia) xi | 4(10) | 20(50) | 16(40) | 45(75) | 15(25) |
| Ia) xii | 4(10) | 20(50) | 16(40) | 50(83) | 10(17) |
| Ia) xiii | 4(10) | 20(50) | 16(40) | 55(92) | 5(8) |
| Ia) xiv | 4(10) | 20(50) | 16(40) | 60(100) | 0(0) |
| Ia) xv | 4(10) | 20(50) | 16(40) | 0(0) | 60(100) |
| Ia) xvi | 16(40) | 8(20) | 16(40) | 60(100) | 0(0) |
| Ia) xvii | 24(60) | 0(0) | 16(40) | 60(100) | 0(0) |
| Ia) xviiii | 3(7.5) | 17(42.5) | 20(50) | 30(50) | 30(50) |
| Ia) xix | 5(12.5) | 25(62.5) | 10(25) | 30(50) | 30(50) |
| Ia) xx | 6.5() | 31.5() | 2(5) | 30(50) | 30(50) |
| Ia) xxi | 8(20) | 16(40) | 16(40) | 40(67) | 20(33) |
| Ia) xxii | 8(20) | 16(40) | 16(40) | 34.5(57.5) | 25.5(42.5) |
| Ia) xxiii | 8(20) | 16(40) | 16(40) | 32(53) | 28(47) |
| Ia) xxiv | 8(20) | 16(40) | 16(40) | 31(52) | 29(48) |
| Ia) xxv | 8(20) | 16(40) | 16(40) | 30(50) | 30(50) |
| Ia) xxvi | 8(20) | 16(40) | 16(40) | 29(48) | 31(52) |
| Ia) xxvii | 8(20) | 16(40) | 16(40) | 27(45) | 33(55) |
| Ia) xxviii | 8(20) | 16(40) | 16(40) | 26(43) | 34(57) |
| Ia) xxix | 8(20) | 16(40) | 16(40) | 60(100) | 0(0) |
| Ia) xxx | 8(20) | 16(40) | 16(40) | 49.5(82.5) | 10.5(17.5) |
| Ia) xxxi | 8(20) | 16(40) | 16(40) | 49(82) | 11(18) |
| Ia) xxxii | 8(20) | 16(40) | 16(40) | 47.5(79) | 12.5(21) |
| Ia) xxxiii | 8(20) | 16(40) | 16(40) | 47(78) | 13(22) |
| Ia) xxxiv | 8(20) | 16(40) | 16(40) | 46.5(78) | 13.5(22) |
| Ia) xxxv | 8(20) | 16(40) | 16(40) | 46(77) | 14(23) |
| Ia) xxxvi | 8(20) | 16(40) | 16(40) | 45(75) | 15(25) |
| Ia) xxxvii | 8(20) | 16(40) | 16(40) | 29(48) | 31(52) |
| Ia) xxxviii | 8(20) | 28(70) | 4(10) | 30(50) | 30(50) |
| Ia) xxxix | 8(20) | 16(40) | 16(40) | 40(67) | 20(33) |
| Ia) xl | 4(10) | 20(50) | 16(40) | 27(45) | 33(55) |
| Ia) xli | 4(10) | 20(50) | 16(40) | 29.5(49) | 30.5(51) |
| Ia) xlii | 12(30) | 12(30) | 16(40) | 35(58) | 25(42) |
| Ia) xliii | 12(30) | 12(30) | 16(40) | 52(87) | 8(13) |
| Ia) xliv | 8(20) | 28(70) | 4(10) | 52(87) | 8(13) |
| Ia) xlv | 16(40) | 8(20) | 16(40) | 59.5(99) | 0.5(1) |
| Ia) xlvi | 8(20) | 16(40) | 16(40) | 30(50) | 30(50) |
| Ia) xlvii | 8(20) | 20(50) | 12(30) | 30(50) | 30(50) |
| Ia) xlviii | 8(20) | 24(60) | 8(20) | 30(50) | 30(50) |
| Ia) xlix | 8(20) | 28(70) | 4(10) | 30(50) | 30(50) |
| Ia) l | 8(20) | 30(75) | 2(5) | 30(50) | 30(50) |
| Ia) li | 7.5(19) | 16(40) | 16.5(41) | 40(67) | 20(33) |
| Ia) lii | 7.5(19) | 16(40) | 16.5(41) | 32(*54) | 27.5(*46) |
| Ia) liii | 7.5(19) | 16.5(21) | 16(40) | 29(*49) | 30.5(*51) |
| Ia) liv | 8(20) | 20(50) | 12(30) | 44.5(*75) | 15(*25) |
| Ia) lv | 7.5(19) | 20(50) | 12.5(31) | 29.5(*) | 30(*) |
| Ia) lvi | 7.5(19) | 24(60) | 8.5(21) | 45(75) | 15(25) |
| Ia) lvii | 7.5(19) | 24(60) | 8.5(21) | 30(50) | 30(50) |
| Ia) lviii | 8(20) | 28(70) | 4(10) | 30(50) | 30(50) |
| Ia) lix | 8(20) | 28(70) | 4(10) | 45(75) | 15(15) |
| Ia) lx | 8(20) | 30(75) | 2(5) | 30(50) | 30(50) |
| Ia) lxi | 8(20) | 30(75) | 2(5) | 45(75) | 15(15) |
| Ia) lxii | 0(0) | 24(60) | 16(40) | 30(50) | 30(50) |

The container with reaction mixture was placed in an ice/water bath, sonicated for 10 min to obtain a clear solution, and then purged with nitrogen for 10 min. Using a 100 µL syringe and a short Teflon sleeve, this polymerization mixture was transferred into 50 cm long capillaries, filling a 35 cm long segment, and the capillaries were then sealed at both ends with rubber stoppers.

Polyimide coated fused silica capillaries having a 100 µm internal diameter (Polymicro Technologies, Phoenix, Ariz.) were used for thermally initiated polymerization. The filled capillaries were submerged in a water bath and allowed to react for 20 h at 60° C.

UV initiated polymerization was carried out in fused silica capillaries having a 100 µm internal diameter and a UV transparent fluorinated hydrocarbon polymer coating (Polymicro Technologies, Phoenix, Ariz.). Capillaries were placed in a box equipped with two 8 W UV lamps (VWR Scientific Products) and irradiated at room temperature for 16 h.

The monolithic capillaries were washed directly with the mobile phase (acetonitrile-methanol 80:20 containing 0.4 mol/L acetic acid and 4 mmol/L triethylamine) to remove unreacted monomers and porogens using a micropump (Model 260D, ISCO, Lincoln, Nebr.). Typically, back pressures of 14–20 MPa (2000 to 3000 psi) were generated at flow rates of 1–3 µL/min. All of the tested columns tolerated these high pressures without extrusion or visible compression of the polymer monolith. The capillaries were then cut at both ends to a total length of 33.5 cm and a bed length of 25 cm, leaving a 8.5 cm long open segment between the detection window and the outlet end. Capillaries with the UV transparent coating were placed in the alignment interface of the cassette, while detection window was first created on polyimide-coated capillaries at the end of the continuous bed using a razor blade.

EXAMPLE 3
Preparation of Monolithic Capillary Column

A monomer mixture is prepared by mixing of 0.6 g 1-methacryloyl-oxyethyl-2-oxy-N-carbamoyl-L-valine-3,5-dimethyl anilide, 1 g ethylene dimethacrylate, and 0.4 g methacrylic acid in which 0.02 g azobisisobutyronitrile is dissolved. Subsequently, 0.5 g cyclohexanol, and 2.5 g 1-dodecanol are admixed to this solution and the mixture purged with nitrogen for 10 min to remove dissolved oxygen.

Using a syringe and a Teflon sleeve, this polymerization mixture is transferred into 50 cm long 100 µm i.d. fused silica capillaries, the ends are sealed, and the contents polymerized in a water bath at a temperature of 60° C. for 20 h.

The capillary column is then attached to a syringe type micropump using typical capillary HPLC fittings. The columns are washed first by pumping methanol through the monolith at a flow rate of 0.1 µL/min for 2 h to remove the unreacted compounds and porogens from pores and then with a 80:20 acetonitrile/phosphate buffer mixture at a flow rate of 0.1 µL/min for 1 h.

The electrophoretic injection of solution containing racemic N-(3,5-dinitrobenzoyl)leucine diallylamide is achieved by applying 5 kV to the sample vial for 3 seconds. The end of the capillary is then inserted into the solvent vial containing a 80:20 acetonitrile/phosphate buffer mixture to achieve the electrochromatographic separations at a voltage of 25 kV. Chromatographic trace obtained by monitoring the UV adsorption during the separation run exhibits two well resolved peaks representing individual enantiomers of the leucine derivative.

EXAMPLE 4
Preparation of Monolithic Capillary Column

A monomer mixture is prepared by mixing of 0.8 g 2-hydroxyethyl methacrylate (N-carbamoyl-L-valine-3,5-dimethyl anilide) carbamate, 0.8 g ethylene dimethacrylate, and 0.4 g glycidyl methacrylate in which 0.02 g azobisisobutyronitrile is dissolved. Subsequently, 0.5 g cyclohexanol, and 2.5 g 1-dodecanol are admixed to this solution and the mixture purged with nitrogen for 10 min to remove dissolved oxygen. This polymerization mixture is transferred into 25 cm long 75 µm i.d. fused silica capillary using a syringe, the ends of this capillary are sealed, and the mixture inside polymerized in a water bath at a temperature of 70° C. for 12 h.

As in Example 3, the capillary column is washed first by pumping methanol through the monolith at a flow rate of 0.1 µL/min for 2 h to remove the unreacted compounds and porogens from its pores. In the next step, a solution prepared by dissolution of 2.7 g trimethylamine and 0.65 g trisodium phosphate in 13 mL water is pumped at a flow rate of 0.25 µL/min for 2 h using the syringe pump while the capillary is placed in a water bath heated to 40° C. to transform the epoxide groups to quaternary trimethyl-2-hydroxypropylammonium functionalities. Once this reaction is completed, the monolith is washed with a mixture of acetonitrile-methanol 80:20 containing 0.4 mol/L acetic acid and 4 mmol/L triethylamine at a flow rate of 0.1 µL/min for 1 h to remove residual compounds from the pores and equilibrate the separation medium.

This monolithic column is used in the same manner as the columns prepared in Example 2.

EXAMPLE 5
Preparation of Bulk Polymer

Various polymeric compositions were prepared according to the method of Example 2. For thermally initiated polymerization, after the glass vials were filled with the polymerization mixture they were submerged in a water bath and allowed to react for 20 h at 60° C. For the UV initiated polymerization, instead of the glass vials used in the thermal process, the polymerization mixture was polymerized in a quartz glass tube sealed with a Teflon film. The tube was placed in a box equipped with two 8 W UV lamps (VWR Scientific Products) and irradiated at room temperature (20° C.) for 16 h. The bulk polymers were crushed to small pieces, Soxhlet extracted with methanol for 12 h, and vacuum dried at 60° C. These polymers were used for the porosimetric measurements and elemental analysis.

EXAMPLE 6
Tandem Synthesis of Monolithic Capillary Columns and Corresponding Bulk Polymer The syntheses of Example 2 for the monolithic capillary columns and of bulk polymer in Example 5 were coordinated so that the polymerization is carried out under substantially the same conditions. For UV initiated polymerization the quartz glass tube was placed in the UV irradiation box for the 16 h (two 8W UV lamps, VWR Scientific) simultaneously with the capillaries filled with the polymerization mixture. For thermal polymerization, after the capillaries were filled with the polymerization mixture, a sealed glass vial containing the remaining polymerization mixture was submerged into a water bath substantially simultaneously with the submersion of the capillaries and allowed to react for 20 h at 60° C. In this manner a polymer forming under substantially similar conditions to the in situ polymerization from polymerization mixture placed in the capillaries is generated as the corresponding bulk polymer. For several polymerization mixture compositions and conditions (Example 2), the in situ formed monolithic capillary column polymer was compared by the methods of Example 7, below, to the corresponding bulk polymer to ascertain correspondence of both elemental composition and physical properties. As expected, the bulk polymers did not differ significantly from their corresponding in situ formed polymers.

EXAMPLE 7

Polymer Characterization

Characterization of Porous Properties. The pore size distributions of the porous monolithic materials from Example 5 were determined using an Autopore III 9400 mercury intrusion porosimeter (Micromeritics, Norcross, Ga.). Specific surface areas were measured by nitrogen adsorption/desorption (ASAP 2010, Micromeritics) and calculated using the Brunauer, Emett, and Teller isotherm (BET) equation, which is known in the art to have theoretical underpinnings in a layering of adsorbed gases at the surface. Scanning electron microscopy (SEM) images were obtained using a JEOL JSM6300 electron microscope. Elemental analysis was performed by standard methods known in the art.

Bulk polymers were compared to their corresponding in situ polymerized polymers from the monolithic capillary columns as described in Example 4, to determine that the bulk polymers were sufficiently similar to their corresponding in situ polymers to characterize the bulk polymers for the remaining polymerizing mixture compositions and polymerization conditions.

EXAMPLE 8

Capillary Electrochromatography (CEC) Experiments

CEC experiments were carried out using a modified HP $^{3D}$CE capillary electrophoresis instrument (Hewlett Packard, Palo Alto, Calif.). The instrument was equipped with a diode array detector and an external pressurization system. An equal pressure of 0.6 MPa (87 psi) was applied at both ends of the capillary column. The sample solutions (0.5 mg/mL) were injected electrokinetically (−15 kV for 5 s), and the separations performed at a voltage of −25 kV and at a temperature of 50° C. or 30° C., as specified. The peaks were monitored at a wavelength of 250 nm and processed by the HP ChemStation software. Acetone was added as an EOF-marker.

Analytes for CEC experiments included: N-3,5-dinitrobenzoyl (DNB), N-benzoyl (Bz), N-acetyl (Ac), N-9-fluorenyl-methoxycarbonyl (Fmoc), N-3,5-dinitrobenzyloxycarbonyl (DNZ), N-benzyloxycarbonyl (Z), and N-2,4-dinitrophenyl (DNP) derivatives of leucine (Leu), valine (Val), phenylalanine (Phe), serine (Ser), and glutamine (Gln). Racemic N-3,5-dinitrobenzoylleucine (DNB-Leu) as well as its (S)-enantiomer were purchased from Aldrich, as were all other racemic analytes used herein for which a preparation method has not been provided. The preparation of N-3,5-dinitrobenzyloxycarbonyl leucine (DNZ-Leu) was carried out as described by Piette et al. (1997) *Chirality* 9:157–161. The solvent for the mobile phase carrying the analytes was performed using acetonitrile-methanol (80:20, v/v), 400 mM acetic acid (0.4 mol/L) and 4 mM (4 mmol/L) triethylamine (TEA), a mobile phase found to optimize enantioselectivity.

EXAMPLE 9

Effect of Porogen Composition and Chiral Monomer on Porous Properties

This example describes the effect of the porogenic solvent and the chiral monomer on the porous properties of the monolithic copolymer. Various compositions of Table 1 were used, i.e., combinations of 1, EDMA, and HEMA or GMA, differing only in the composition of the binary porogenic solvent (i.e., cyclohexanol and 1-dodecanol). Monolithic capillary columns were prepared according to Example 2, using both UV and thermally initiated polymerization, and corresponding bulk copolymers were prepared as described in Examples 5 and 6. Physical measurements including pore size distribution (modes reported) and specific surface area from BET isothermal condensation analysis were carried out according to Example 7.

Figure 2A:
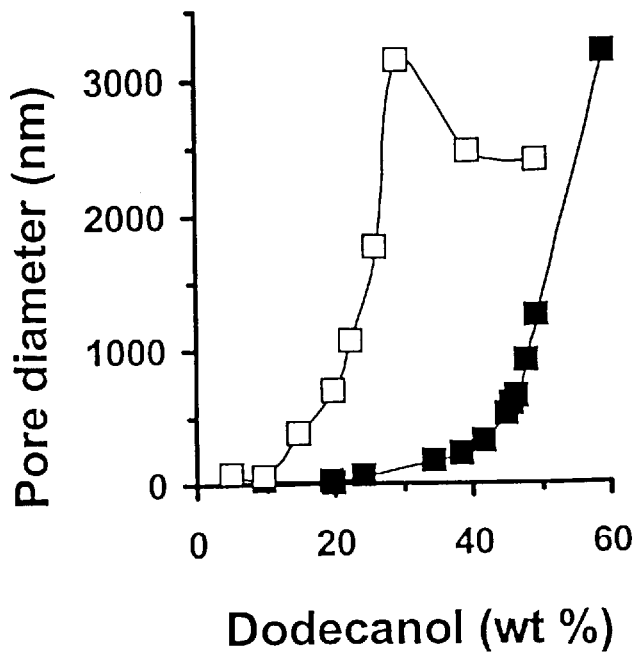
FIGS. 2A and 2B illustrate in graph form the effect of thermal (FIG. 2A) and UV initiation (FIG. 2B), type of comonomer, and percentage of 1-dodecanol in the polymerization mixture on the mode pore diameter of quinidine-functionalized chiral monoliths, as evaluated in Example 9 (in the figures, □ represents glycidyl methacrylate, and ■ represents 2-hydroxyethyl methacrylate).
Figure 2B:
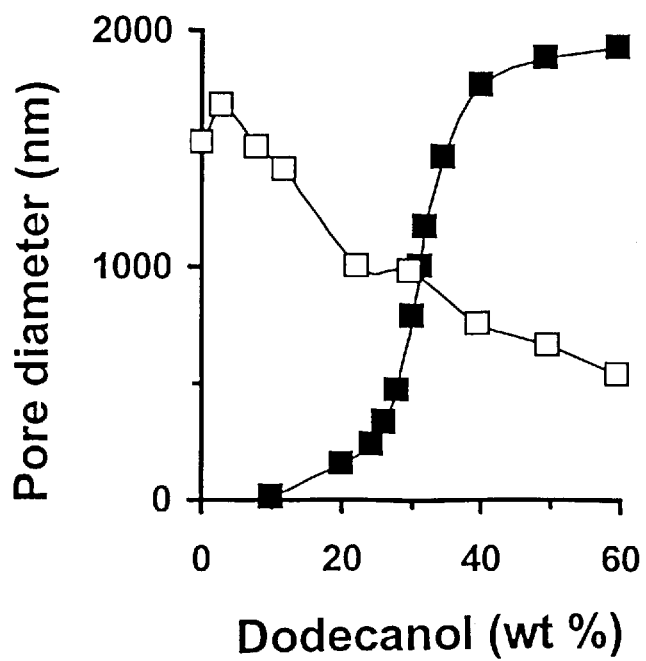

FIGS. 2A and 2B show the effect of dodecanol content in the porogenic solvent mixture on mode pore size (pore diameter at the maximum of the distribution curve) for monoliths prepared from mixtures containing 8 wt. % GMA or HEMA as a comonomer using either thermal (FIG. 2A) or UV (FIG. 2B) initiation (in the figures, □ represents glycidyl methacrylate, and ■ represents 2-hydroxyethyl methacrylate), 16 wt. % ethylene dimethacrylate, and 60 wt. % porogenic solvent. Both the nature of the comonomer as well as the initiation method affected the porous structure. Compared to GMA-containing monoliths, a much higher content of dodecanol in the dodecanol/cyclohexanol mixture was generally required to obtain HEMA containing monoliths with sufficiently large pores for bulk flow required for CEC separations. For example, GMA monoliths with a mode pore size of 1,000 nm were obtained by thermal polymerization at 60° C. using a polymerization mixture containing 20% dodecanol and 40% cyclohexanol. In contrast, a much higher percentage of the less polar and more hydrophobic dodecanol (50%) was required for the preparation of HEMA containing monoliths with a similar pore size (see FIG. 2A).

Photoinitiated polymerization of the same mixtures at 20° C. generally yielded monoliths with larger pores compared to those initiated thermally (see FIG. 2B). Thus, the dodecanol content in the polymerization mixture used for UV initiated polymerizations had to be reduced in order to obtain pore sizes comparable to those of their thermally polymerized analogs. For example, a polymerization mixture containing only 30% dodecanol produces a monolith with 1,000 nm pores by UV polymerization when HEMA was used as the comonomer. These shifts can readily be explained by the effect of the polymerization temperature, since the creation of larger pores is favored at lower temperatures.

Figure 3A:
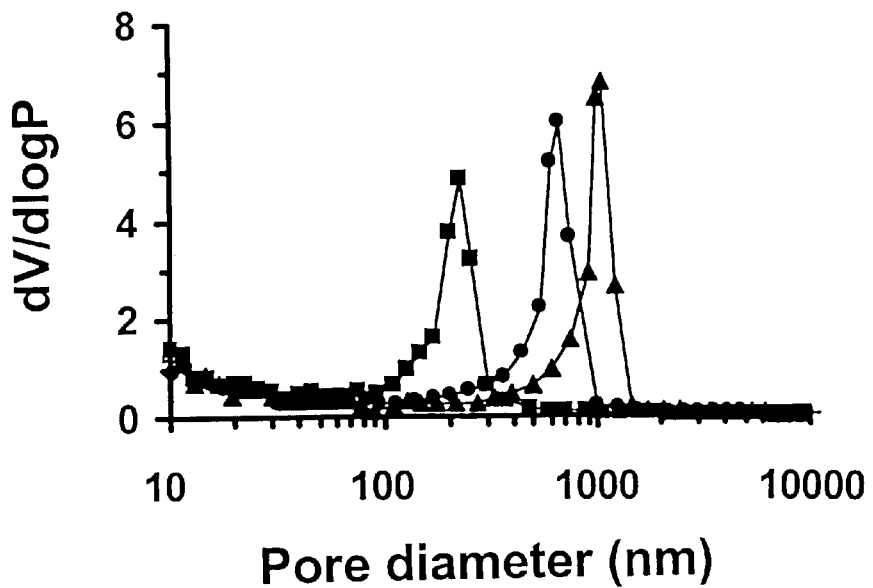
FIGS. 3A and 3B illustrate the differential pore size distribution profiles of poly (1-co-hydroxyethyl methacrylate-co-ethylene dimethacrylate) monoliths prepared using thermal (FIG. 3A) and UV initiated (FIG. 3B) polymerization, as evaluated in Example 9.
Figure 3B:
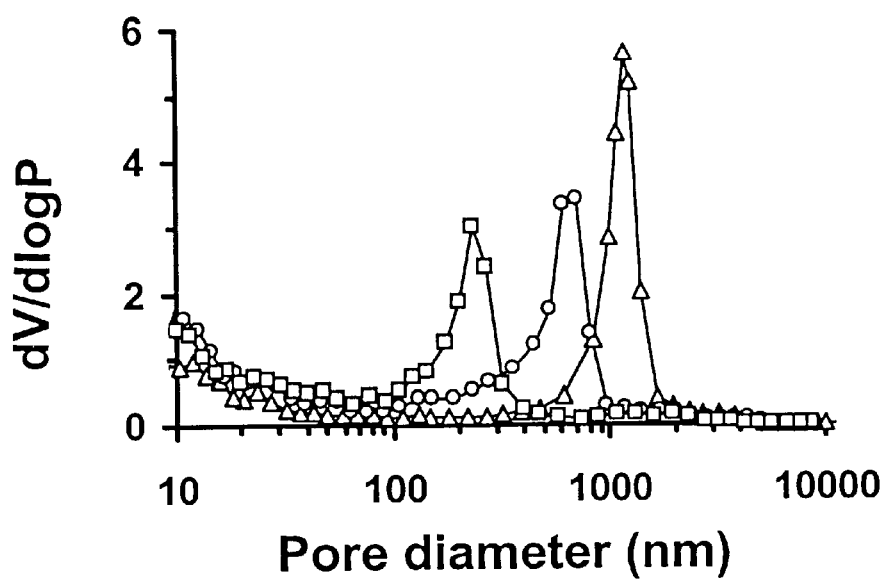

The physical properties of the quinidine-functionalized HEMA monoliths prepared both by UV and thermally initiated polymerization indicate that good control of pore size can be exerted over a rather broad range. As expected, the specific surface areas ranging from 1 to 15 m²/g were inversely proportional to the pore size. It should be noted that the porosity profile of UV and thermally polymerized monoliths prepared from the same monomer mixture were not substantially different; see FIGS. 3A and 3B, which show the similar pore size distribution profiles obtained for the monolith prepared using thermal initiation (FIG. 3A) and for the monolith prepared using UV initiation (FIG. 3B) (porogenic solvent consisting of 39 (■), 47 (●), 50 (▲), 25 (□), 29 (○), and 32 (△) wt. % 1-dodecanol) As may be seen, the curves were unimodal with one distinct maximum in the macropore range regardless of the preparation procedure.

Figure 4A:
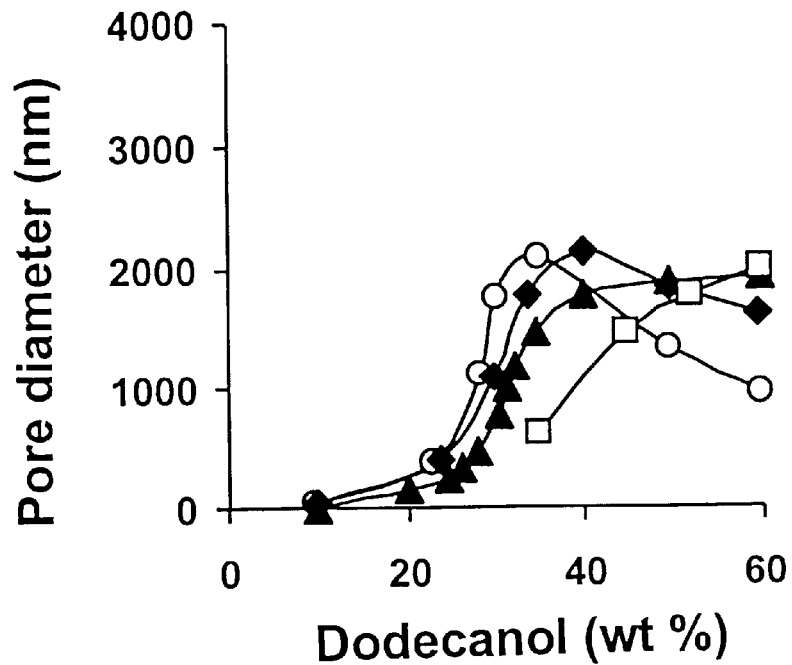
FIGS. 4A and 4B illustrate the effect of the percentage of chiral monomer 1 on pore size of the monoliths prepared using UV initiated (FIG. 4A) and thermally initiated (FIG. 4B) polymerization, as described in Example 9.
Figure 4B:
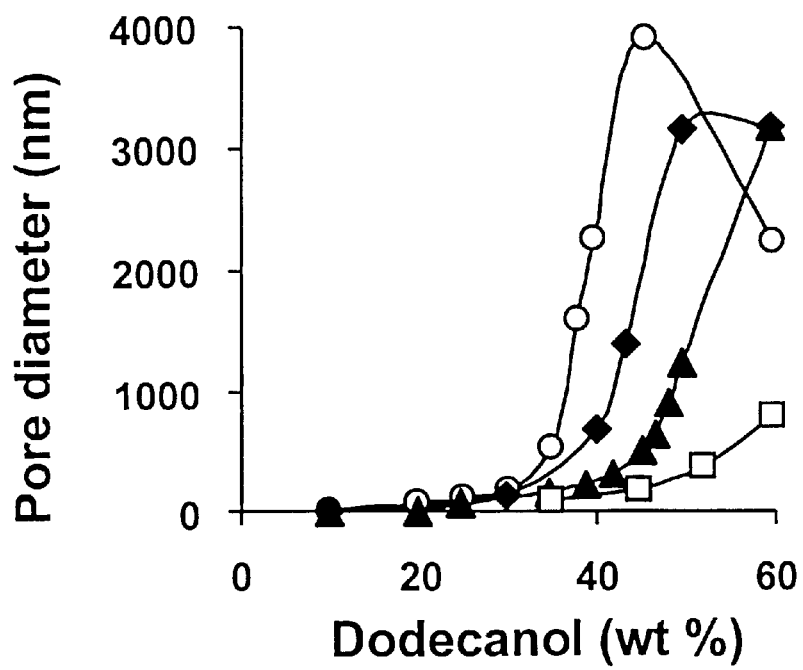

The porous properties of the monoliths also depend on the percentage of chiral monomer in the polymerization mixture. As shown in FIGS. 4A and 4B for both photoinitiated (FIG. 4A) and thermally initiated polymerizations (FIG. 4B), an increase in the percentage of chiral monomer 1 in the polymerization mixture at a fixed composition of porogen lead to a significant decrease in the pore size (in the figures, the amount of chiral monomer is 0 (○), 4 (♦), 8 (▲), or 12 (□) wt. %). For example, a photopolymerized monolith with a mode pore diameter of 1,600 nm is obtained using a mixture consisting of 4% 1 and 20% HEMA, in addition to 16% EDMA, 35% 1-dodecanol, and 25% cyclohexanol (composition Ia)ii, Table 1, Example 2). Monoliths with smaller pore diameters of 1,400 and 600 nm were obtained when the percentage of 1 was increased to 8% and 12% respectively, with a concomitant decrease in HEMA (FIG. 4A). Although the thermally initiated system behaved slightly differently, the overall effects were very similar as shown in FIG. 4B.

EXAMPLE 10
Characterizing Flow in Monoliths Under CEC Conditions

Figure 5:
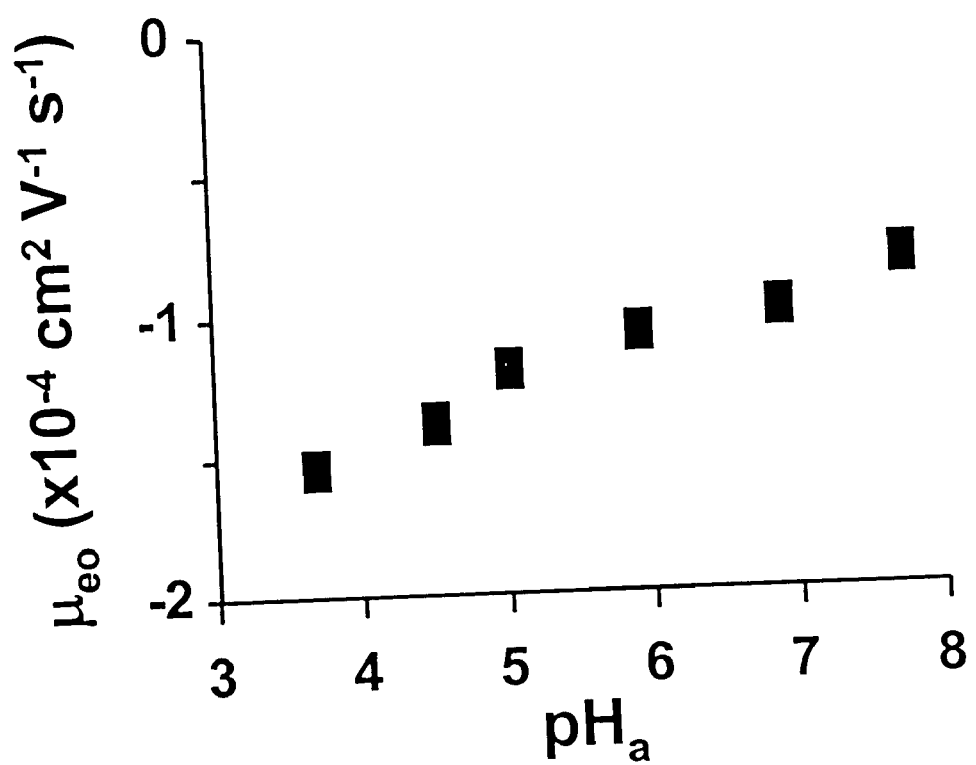
FIG. 5 illustrates the effect of pH of the mobile phase on electroosmotic mobility in quinidine-functionalized chiral monoliths, as evaluated in Example 10.

The quinidine moieties of the chiral monomer prepared in Example 1 and used to prepare the copolymer 1 as described in Example 2 contains two basic sites: (i) quinoline, which is an aromatic amine; and (ii) a quinuclidine moiety, with a tertiary amine group. The $pK_a$ values for these groups are reported to be 5.4 and 10.0, respectively. As a result, the chiral monolithic columns operate best in acidic mobile phases, since the monolith surface is positively charged under these conditions. Due to the cationic nature of the quinidine functionality, the positive ζ-potential drives EOF towards the anode. FIG. 5 shows the effect of the pH of the mobile phase on electroosmotic mobility ($\mu_{eo}$) (FIG. 5 conditions—polymerization mixture, chiral monomer 8 wt. %, 2-hydroxyethyl methacrylate, 16 wt. %; UV-initiated polymerization for 16 h at room temperature; capillary column 335 nm (250 active length)×0.1 mm i.d.; EOF marker, acetone; mobile phase 80:20 acetonitrile-0.1 mol/L 4-morpholinoethanesulfonic acid; apparent pH adjusted with triethylamine; voltage, −15 kV; separation temperature 20° C., injection at −5 kV for 5 s). The monolithic stationary phase is a weak anion exchanger, the ionization and consequently the electroosmotic flow vary within the studied pH range in relation to the $pK_a$ values of the charged sites. The negative values of $\mu_{eo}$ indicate that the anodic flow increases as the protonation of the weak anion exchange functionalities increases. It should be pointed out that anodic flow is advantageous in the separation of anionic analytes, since both electroosmotic and electrophoretic transports have the same direction and the electrophoretic migration may help to accelerate the separation.

EXAMPLE 11
Accelerating Chromatographic Enantioselective Separations

Figure 6A:
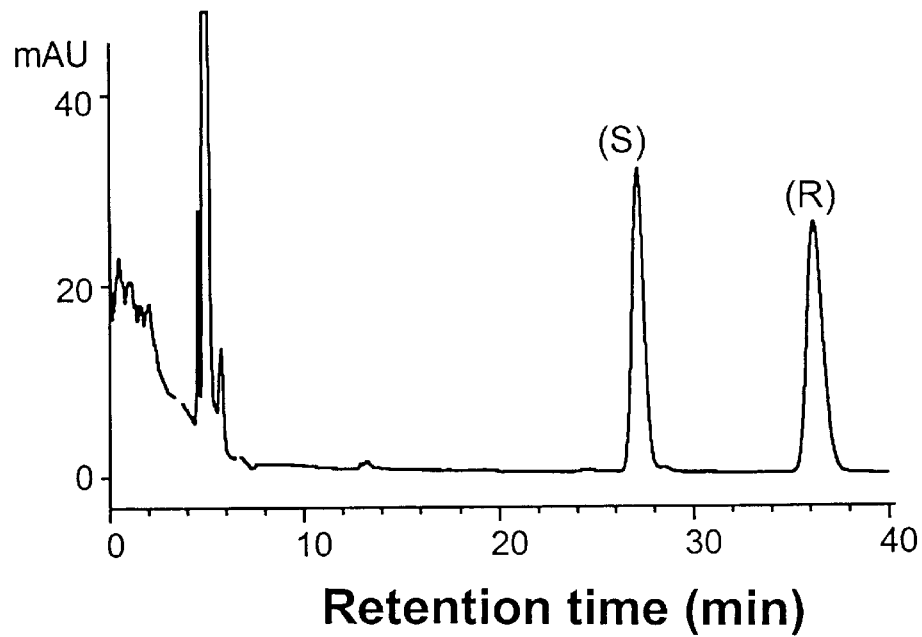
FIGS. 6A, 6B and 6C illustrate the enantioseparation of N-3,5-dinitrobenzyloxycarbonyl (DNZ)-leucine on standard columns with 25 cm (FIG. 6A), 15 cm (FIG. 6B), and 8.5 cm (FIG. 6C) long monolith, carried out as described in Example 11.
Figure 6B:
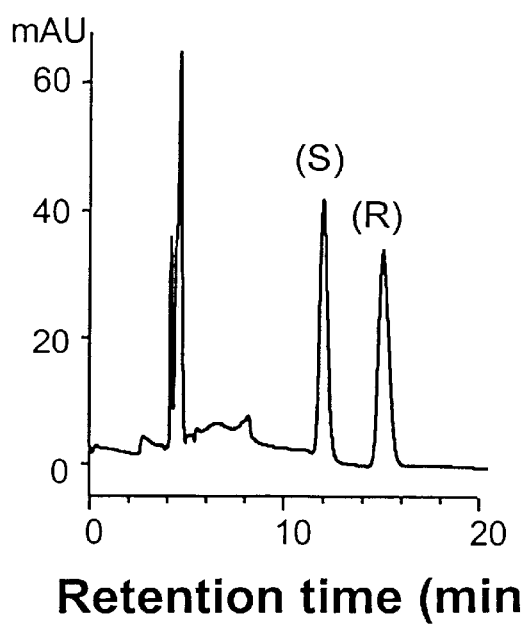

Strong selector-analyte interactions are required to obtain suitable enantioselectivity. In CEC, this is often accompanied by relatively long run times for columns with the standard bed lengths of 25 cm that is dictated by requirements of the common HP $^{3D}$CE instrumentation. Since the resolution of the monolithic capillary columns of the invention is sufficiently high, the long run times can be decreased by reducing the length of the monolithic segment while increasing the length of the open segment. This is demonstrated in FIGS. 6A, 6B and 6C, which illustrate the enantioseparation of DNZ-(R,S)-Leu on standard columns with 25 cm (FIG. 6A), 15 cm (FIG. 6B), and 8.5 cm (FIG. 6C) long monoliths (conditions: chiral monomer 1, 12 wt. %, 2-hydroxyethyl methacrylate, 20 wt. %, ethylene dimethacrylate, 8 wt. %, 1-dodecanol, 50 wt. %, and cyclohexanol, 10 wt. %; UV-initiated polymerization for 16 h at ambient temperature; capillary columns 335 mm×0.1 mm i.d., active length 250 mm; mobile phase 0.4 mol/L acetic acid and 4 mmol/L triethylamine in 80:20 mixture of acetonitrile and methanol; separation temperature 50° C.; voltage, −30 kV, injection at −15 kV for 5 s).

The method of Example 2 can be readily modified to prepare a column having a shorter bed length by infusing a smaller amount of the polymerization mixture into each capillary. This would allow for a decrease in separation time while still obtaining a sufficiently effective separation of the desired stereoisomers.

Figure 6C:
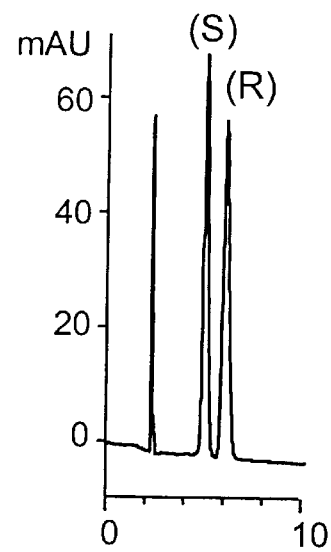

For example, a reduction of the monolithic bed length from 25 to 15 cm results in a decrease in run time from 40 to 16 min for the enantioseparation of DNZ-Leu. Although the resolution $R_S$ of 3.55 is lower than that of 6.78 for the 25 cm column, it is still sufficient for a very good separation as demonstrated in FIG. 6B. A further reduction in the length of the monolithic segment to 8.5 cm affords $R_S$=2.03, which is still adequate for practical application and also reduces the run time to only 7 min (FIG. 6C).

Figure 7A:
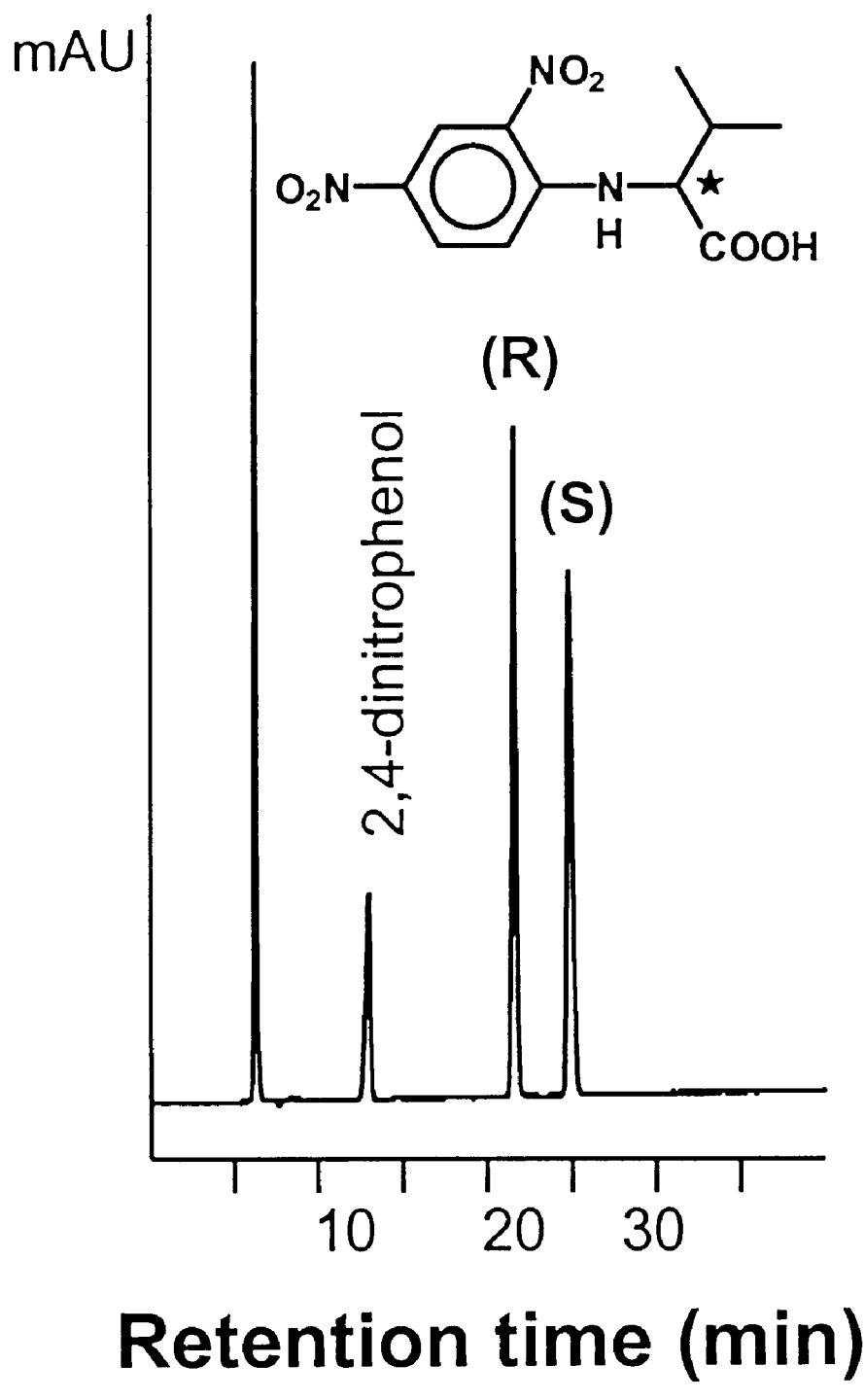
FIGS. 7A, 7B and 7C illustrate CEC separations of N-2,4-dinitrophenyl (DNP)-valine (FIG. 7A), N-benzoyl (Bz)-leucine (FIG. 7B), and Fenoprop (FIG. 7C) enantiomers on a 150 mm long quinidine-functionalized chiral monolith, as described in Example 12.
Figure 7B:
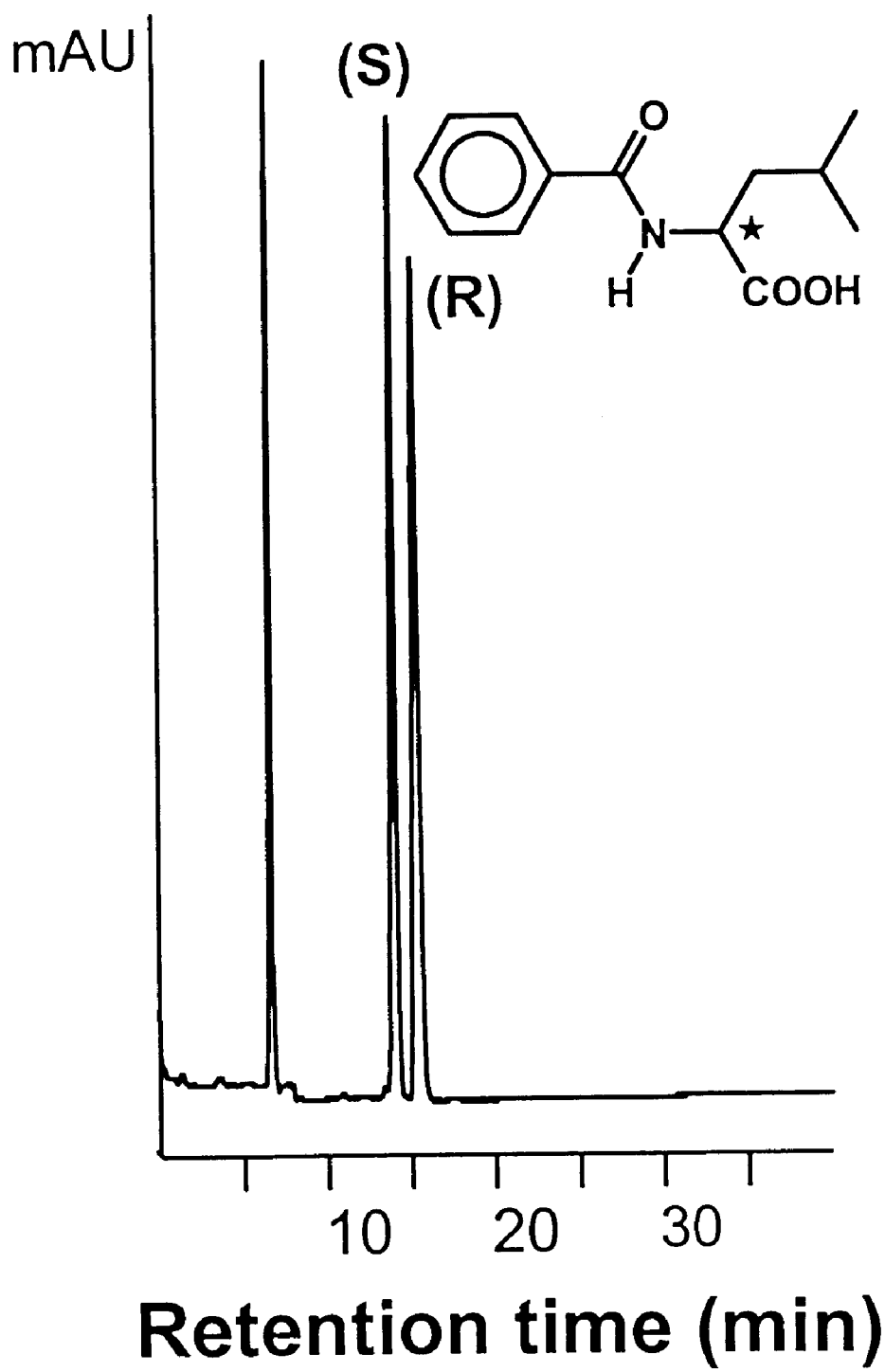
Figure 7C:
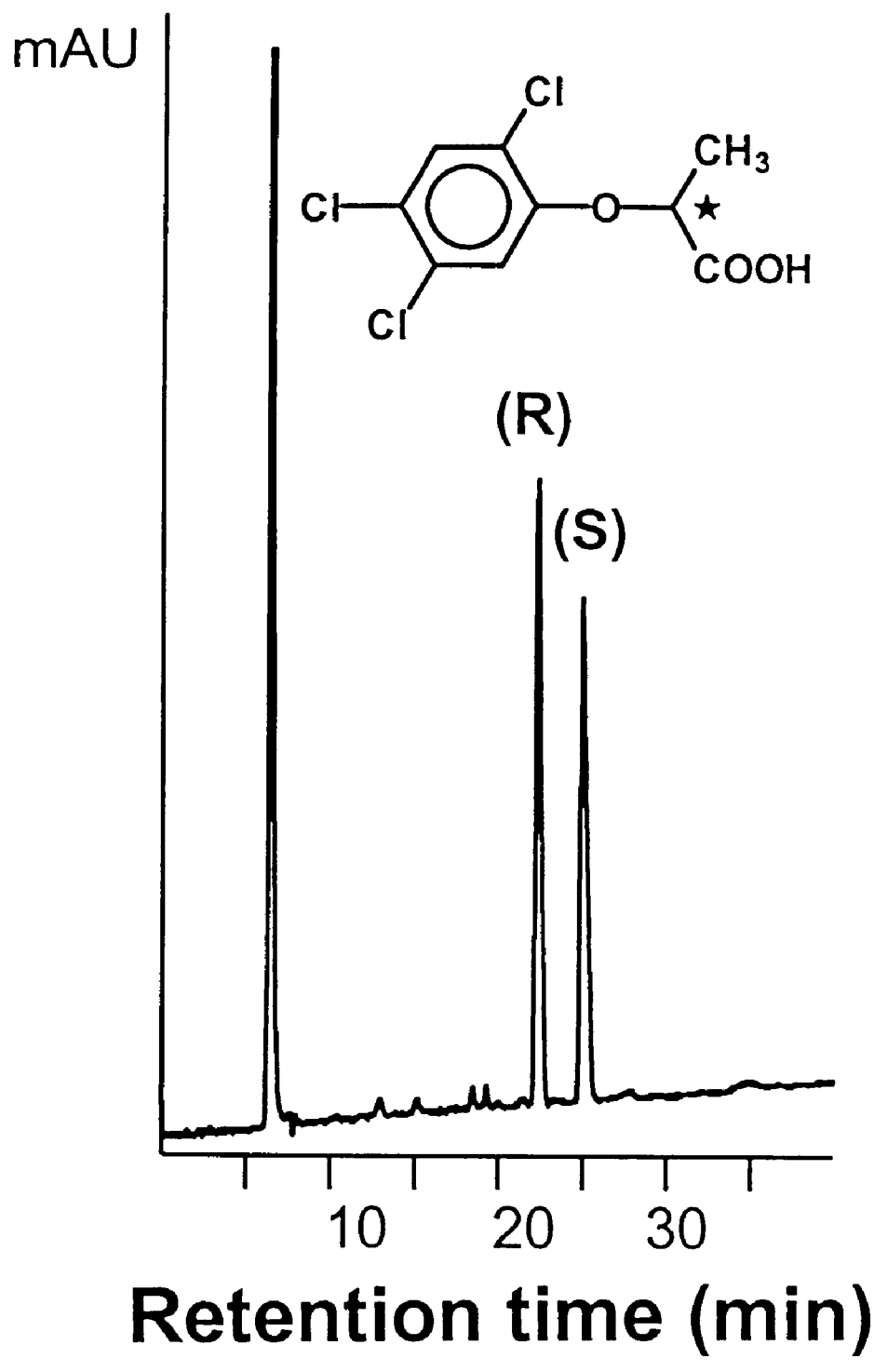

EXAMPLE 12
Specific, Practicable and Optimized Chromatographic Enantioselective Separations Experiments according to Example 8, using monolithic capillary columns prepared according to Example 2 and exemplified in the preceding examples, may be used to optimize separations of chiral analytes. The results obtained show the separation of a variety of enantiomers of racemic analytes using a quinidine-functionalized monolithic column crosslinked with 16% ethylene dimethacrylate and optimized chromatographic conditions. Good enantioselectivity and excellent efficiencies were observed for a number of derivatized amino acids. For example, FIG. 7A shows the separation of racemic DNP-Val for which very high efficiencies of 242,400 and 193,700 plates/m were achieved for the first and second eluting enantiomer, respectively. To the best of applicants' knowledge, this is currently the highest efficiency reported for enantioselective electrochromatography and reaches the levels heretofore reached only with capillary electrophoresis. This chiral monolithic column also enables the separation of analytes that do not contain a strong π-acidic functionality such as N-benzoyl leucine (FIG. 7B) with a good selectivity. In addition, molecules such as the α-aryloxycarboxylic acid herbicides Mecoprop and Fenoprop were also well separated. FIG. 7C shows as an example the separation of two Fenoprop enantiomers with efficiencies of 153,200 and 123,100 plates/m (FIGS. 7A–7C, conditions: chiral monomer 1, 8 wt. %, 2-hydroxyethyl methacrylate, 28 wt. %, ethylene dimethacrylate, 4 wt. %, 1-dodecanol, 30 wt. %, and cyclohexanol, 30 wt. %; UV-initiated polymerization for 16 h at ambient temperature; capillary columns 335 mm×0.1 mm i.d., active length 250 mm; mobile phase 0.6 mol/L acetic acid and 6 mmol/L triethylamine in 80:20 mixture of acetonitrile and methanol; separation temperature 50° C.; voltage, −25 kV).

EXAMPLE 13
Microfabricated Device with Monolithic Polymer for Enantioseparation

A monomer mixture is prepared by mixing of 1.2 g O-[2-(methacryloyloxy)ethylcarbamoyl]-10,11-dihydroquinidine, 2 g ethylene dimethacrylate, and 0.8 g 2-hydroxyethyl methacrylate in which 0.04 g azobisisobutyronitrile is dissolved. Subsequently, 1 g cyclohexanol, and 5 g 1-dodecanol is admixed to this solution and the mixture purged with nitrogen for 10 min to remove dissolved oxygen and afford stock polymerization mixture suitable for the preparation of a monolithic material. This mixture can be kept in a freezer for several weeks without changing its polymerizability.

Using a syringe, two parallel 5 cm long, 70 μm wide, and 20 μm deep channels located within a planar glass microchip are filled with this polymerization mixture. The upper part of this chip is then covered with a mask that covers all the surface of the chip except for the separation channels. This "sandwich" is placed into a box equipped with two 8 W UV lamps and the polymerization allowed to proceed for 16 h.

A metallic holder with specifically localized threaded holes is attached to the chip and connected through a 100 μm i.d. capillary using typical capillary HPLC fittings to a micropump. The monoliths are washed with methanol using pressurized flow at a flow rate of 50 nL/min for 2 h to remove the unreacted compounds and porogens from pores and with a 80:20 acetonitrile-methanol mixture containing 0.4 mol/L acetic acid and 0.004 mol/L triethylamine at a flow rate of 50 nL/min for 1 h. Finally, plastic tubes acting as containers are glued to each hole at the face side of the chip.

This monolith is adjusted at the optical table of the testing unit consisting of a DC power supply, a He/Cd laser, and a photomultplier, and each container provided with a platinum wire electrode. The sample containers are filled with a solution of 4-chloro-7-nitrobenz-2-oxa-1,3-diazole (NBD) labeled D,L-valine and D,L-leucine in the mobile phase, respectively, while the bulk mobile phase (80:20 acetonitrile-methanol mixture containing 0.4 mol/L acetic acid and 0.004 mol/L triethylamine) is placed in the solvent containers. The electrophoretic injection of the samples is achieved by applying −15 kV to the sample containers for 5 seconds. The voltage is then switched to the solvent containers to carry out the electrochromatographic separations. The separated enantiomers are detected by laser induced fluorescence emission. The intensity of fluorescence at 510 nm is monitored. Chromatograms obtained from each channel show two well resolved peaks representing separated individual enantiomers.

What is claimed is:

1. A device for use in conducting chiral electrochromatography, comprising an electrochromatographic conduit within which is an enantioselective separation medium comprised of a monolithic, ionizable copolymer that acts as a continuous separation medium and contains pendant chiral selector groups, wherein the pendant chiral selector groups each contain a stereogenic center.

2. The device of claim 1, wherein the monolithic, ionizable copolymer is a porous organic polymer.

3. The device of claim 1, comprising a capillary tube containing the enantioselective separation medium.

4. The device of claim 1, comprising an electrochromatographic column containing the enantioselective separation medium.

5. The device of claim 1, comprising a microfluidic separation device.

6. The device of claim 5, wherein the conduit is a microchannel containing the enantioselective separation medium.

7. The device of claim 6, wherein the microchannel is tubular.

8. The device of claim 6, wherein the microchannel is planar.

9. The device of claim 5, comprising two or more conduits.

10. The device of claim 9, wherein each conduit is a microchannel containing the enantioselective separation medium.

11. The device of claim 1, wherein the monolith is fabricated by in situ polymerization within the conduit.

12. The device of claim 11, wherein the in situ polymerization is carried out by copolymerization of a mixture comprised of an ionizable chiral monomer, a crosslinking comonomer, a polymerization initiator, and a porogenic solvent.

13. The device of claim 12, wherein the mixture further comprises a functional monovinyl comonomer.

14. The device of claim 13, wherein the functional monovinyl comonomer contains a hydrophilic group or a precursor to a hydrophilic group.

15. The device of claim 11, wherein the in situ polymerization is carried out by copolymerization of a mixture comprised of a chiral monomer, an ionizable comonomer, a crosslinking comonomer, a polymerization initiator, and a porogenic solvent.

16. The device of claim 15, wherein the mixture further comprises a functional monovinyl comonomer.

17. The device of claim 16, wherein the functional monovinyl comonomer contains a hydrophilic group or a precursor to a hydrophilic group.

18. A method for making an electrochromatographic device useful in conducting enantioselective separations, comprising:
   admixing an ionizable chiral monomer with a crosslinking comonomer and a polymerization initiator in a porogenic solvent, to form a polymerization mixture;
   introducing the polymerization mixture into a capillary tube; and
   applying heat or radiation to the polymerization mixture to initiate polymerization, thereby providing a monolithic enantioselective separation medium within the capillary tube.

19. A method for making an electrochromatographic device useful in conducting enantioselective separations, comprising:
   admixing a chiral monomer with an ionizable comonomer, a crosslinking comonomer and a polymerization initiator in a porogenic solvent, to form a polymerization mixture;
   introducing the polymerization mixture into a capillary tube; and
   applying heat or radiation to the polymerization mixture to initiate polymerization, thereby providing a monolithic enantioselective separation medium within the capillary tube.

20. A method for making a microelectrochromatographic device useful in conducting enantioselective separations, comprising:
   admixing an ionizable chiral monomer with a crosslinking comonomer and a polymerization initiator in a porogenic solvent, to form a polymerization mixture;
   introducing the polymerization mixture into a microchannel of a microfluidic separation device; and
   applying heat or radiation to the polymerization mixture to initiate polymerization, thereby providing a monolithic enantioselective separation medium within the microchannel.

21. A method for making a microelectrochromatographic device useful in conducting enantioselective separations, comprising:
   admixing a chiral monomer with an ionizable comonomer, a crosslinking comonomer and a polymerization initiator in a porogenic solvent, to form a polymerization mixture;
   introducing the polymerization mixture into a microchannel of a microfluidic separation device; and applying heat or radiation to the polymerization mixture to initiate polymerization, thereby providing a monolithic enantioselective separation medium within the microchannel.

22. The method of any one of claim 18, 19, 20 or 21, wherein the polymerization mixture further includes a functional monovinyl comonomer.

23. The method of claim 22, wherein the functional monovinyl comonomer contains a hydrophilic group or a precursor to a hydrophilic group.

24. The method of claim 18, 19, 20 or 21, further comprising ionizing the ionizable groups by passing an ionizing composition through the monolithic enantioselective separation medium.

25. The method of claim 24, wherein the ionizing composition is a buffer solution.

26. The method of claim 24, wherein the ionizing composition is a chemical reagent capable of ionizing the ionizable groups.

27. A chiral copolymer suitable for electrochromatographic resolution of racemic compounds, prepared by copolymerization of a mixture comprising (a) an ionizable chiral monomer, (b) a crosslinking comonomer, (c) a polymerization initiator, and (d) a porogenic solvent.

28. The chiral copolymer of claim 27, wherein the ionizable chiral monomer is an addition polymerizable monomer containing a pendant chiral selector moiety.

29. The chiral copolymer of claim 28, wherein the ionizable chiral monomer is a vinyl monomer.

30. The chiral copolymer of claim 29, wherein the ionizable chiral monomer is an acrylate or methacrylate having a pendant chiral selector moiety selected from the group consisting of cinchona alkaloids, 4-substituted dihydropyrimidines, 1,4-disubstituted dihydropyrimidines, 1,2-disubstituted cycloalkanes, amino acids, derivatives thereof, and combinations of any of the foregoing.

31. The chiral copolymer of claim 30, wherein the pendant chiral selector moiety is a cinchona alkaloid.

32. A chiral copolymer suitable for electrochromatographic resolution of racemic compounds, prepared by copolymerization of a mixture comprising (a) a chiral monomer, (b) an ionizable comonomer, (c) a crosslinking comonomer, (d) a polymerization initiator, and (e) a porogenic solvent.

33. The chiral copolymer of claim 32, wherein the chiral monomer is an addition polymerizable monomer having a pendant chiral selector moiety.

34. The chiral copolymer of claim 33, wherein the chiral monomer is a vinyl monomer.

35. The chiral copolymer of claim 34, wherein the chiral monomer is an acrylate or methacrylate having a pendant chiral selector moiety selected from the group consisting of cinchona alkaloids, 4-substituted dihydropyrimidines, 1,4-disubstituted dihydropyrimidines, 1,2-disubstituted cycloalkanes, amino acids, derivatives thereof, and combinations of any of the foregoing.

36. The chiral copolymer of claim 34, wherein the pendant chiral selector moiety is selected from the group consisting of carbohydrates, amino acids, alcohols, amines, thiols, peptides, derivatives thereof, and combinations of any of the foregoing.

37. The chiral copolymer of claim 36, wherein the ionizable comonomer is selected from the group consisting of acrylic or methacrylic acid, itaconic acid, maleic anhydride, acrylic and methacrylic amides of amino acids, 2-vinylpyridine, 4-vinylpyridine, 2-(dialkylamino)ethyl acrylate and methacrylate, 2-(morpholino)ethyl acrylate and methacrylate, glycidyl acrylate and methacrylate, and combinations thereof.

38. The chiral copolymer of claim 32, wherein the ionizable comonomer is a vinyl monomer.

39. The chiral copolymer of claim 38, wherein the ionizable monomer includes an amino group or a carboxylic acid group.

40. The chiral copolymer of claim 27 or 32, wherein the crosslinking comonomer is a polyvinyl monomer.

41. The chiral copolymer of claim 40, wherein the polyvinyl comonomer is a lower alkylene or lower alkanol diacrylate, dimethacrylate, triacrylate or trimethacrylate.

42. The chiral copolymer of claim 41, wherein the polyvinyl comonomer is ethylene diacrylate, ethylene dimethacrylate, trimethylolpropane triacrylate, or trimethylolpropane trimethacrylate.

43. The chiral copolymer of claim 27 or 32, wherein the mixture further comprises a functional monovinyl comonomer.

44. The chiral copolymer of claim 43, wherein the functional monovinyl comonomer contains a hydrophilic group or a precursor to a hydrophilic group.

45. The chiral copolymer of claim 44, wherein the functional monovinyl comonomer is selected from the group consisting of 2-hydroxyethyl methacrylate, 2-hydroxyethyl acrylate, glycidyl methacrylate, glycidyl acrylate, and combinations thereof.

46. A method for preparing a chiral copolymer useful as an enantioselective separation material, wherein the method comprises admixing an ionizable chiral monomer with a crosslinking comonomer and a polymerization initiator in a porogenic solvent, to form a polymerization mixture, and applying heat or radiation to the polymerization mixture to initiate polymerization.

47. A method for preparing a chiral copolymer useful as an enantioselective separation material, wherein the method comprises admixing a chiral monomer with an ionizable comonomer, a crosslinking comonomer and a polymerization initiator in a porogenic solvent, to form a polymerization mixture, and applying heat or radiation to the polymerization mixture to initiate polymerization.

48. The method of claim 46 or 47, wherein the polymerization mixture further includes a functional monovinyl comonomer.

49. The method of claim 48, wherein the functional monovinyl comonomer contains a hydrophilic group or a precursor to a hydrophilic group.

* * * * *

UNITED STATES PATENT AND TRADEMARK OFFICE
CERTIFICATE OF CORRECTION

PATENT NO. : 6,616,825 B1
DATED : September 9, 2003
INVENTOR(S) : Jean M.J. Fréchet et al.

It is certified that error appears in the above-identified patent and that said Letters Patent is hereby corrected as shown below:

<u>Title page,</u>
Item [*] Notice, please replace with the following:
-- Subject to any disclaimer, the term of this patent is extended or adjusted under 35 U.S.C. 154(b) by 318 days. --

Signed and Sealed this

Twentieth Day of July, 2004

JON W. DUDAS
*Acting Director of the United States Patent and Trademark Office*